United States Patent
Ono et al.

(10) Patent No.: US 8,003,666 B2
(45) Date of Patent: Aug. 23, 2011

(54) HYDRATE FOR MEDICAL PURPOSES

(75) Inventors: Makoto Ono, Edogawa-ku (JP); Shoko Yoshida, Edogawa-ku (JP)

(73) Assignee: Daiichi Sankyo Company, Limited, Tokyo (JP)

( * ) Notice: Subject to any disclaimer, the term of this patent is extended or adjusted under 35 U.S.C. 154(b) by 217 days.

(21) Appl. No.: 12/293,827

(22) PCT Filed: Mar. 27, 2007

(86) PCT No.: PCT/JP2007/000304
§ 371 (c)(1),
(2), (4) Date: Sep. 22, 2008

(87) PCT Pub. No.: WO2007/111023
PCT Pub. Date: Oct. 4, 2007

(65) Prior Publication Data
US 2010/0234410 A1   Sep. 16, 2010

(30) Foreign Application Priority Data
Mar. 27, 2006   (JP) ................ 2006-084708

(51) Int. Cl.
*C07D 215/38*   (2006.01)
*A61K 31/04*   (2006.01)

(52) U.S. Cl. ...................... 514/312; 546/156

(58) Field of Classification Search ............ 546/156; 514/312
See application file for complete search history.

(56) References Cited

U.S. PATENT DOCUMENTS

| | | | |
|---|---|---|---|
| 5,587,386 A | 12/1996 | Hayakawa et al. | |
| 6,900,225 B2 * | 5/2005 | Takemura et al. | 514/312 |
| 7,563,805 B2 | 7/2009 | Takahashi et al. | |

FOREIGN PATENT DOCUMENTS

| | | |
|---|---|---|
| JP | 2 231475 | 9/1990 |
| JP | 2002 255962 | 9/2002 |
| JP | 2005-146386 | 5/2005 |
| WO | 2003/076428 * | 9/2003 |
| WO | 2006 123767 | 11/2006 |
| WO | 2006 123792 | 11/2006 |
| WO | WO 2006/123792 A1 | 11/2006 |

OTHER PUBLICATIONS

Bozdogan, J Antimicrobial Chemotherapy, vol. 52, pp. 864-868, 2003.*

* cited by examiner

*Primary Examiner* — D Seaman
(74) *Attorney, Agent, or Firm* — Oblon, Spivak, McClelland, Maier & Neustadt, L.L.P.

(57) ABSTRACT

The present invention relates to [7-[(7S)-7-amino-7-methyl-5-azaspiro[2.4]heptan-5-yl]-6-fluoro-1-[(1R,2S)-2-fluoro-cyclopropyl]-8-methoxy-1,4-dihydro-4-oxoquinoline-3-carboxylic acid hemihydrate. This hemihydrate is stable and easy to prepare, and has excellent properties for a pharmaceutical bulk powder.

14 Claims, 7 Drawing Sheets

\* : P <0.05, \*\*\* : P <0.001 vs Untreated Control
\# : P <0.05, \#\# : P <0.01 vs Bacterial Count in Bladder
at Beginning of Treatment

HYDRATE FOR MEDICAL PURPOSES

CROSS-REFERENCE TO RELATED APPLICATIONS

This application is a 371 of PCT/JP07/00304 filed Mar. 27, 2007 and claims the benefit of JP 2006-084708.

BACKGROUND OF THE INVENTION

1. Field of the Invention

The present invention relates to a compound suitable for a pharmaceutical bulk powder which is used for manufacturing pharmaceutical preparations, in particular, solid preparations.

2. Description of the Related Art

Formula (I):

[Formula 1]

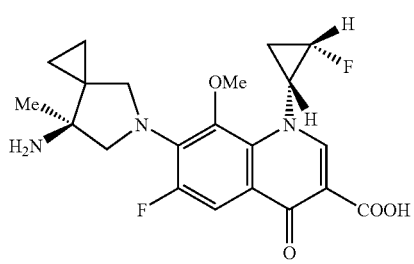

(I)

A novel quinolone compound having the above structure is expected as a synthetic quinolone antibacterial agent having excellent properties, as a medicament that is especially active against not only gram-negative bacteria but also gram-positive bacteria which show low sensitivity to quinolone antibacterial agents, and has excellent safety and pharmacokinetics (JP-A-2005-146386).

In order to provide a compound as a medicament, a compound (or crystalline) having properties suitable for a pharmaceutical bulk powder, which has properties to be processed into various types of preparations, in particular, solid preparations, is required. Such a compound is required to have an excellent stability, such that the compound is required to have an excellent chemical stability, not to absorb and desorb moisture, or not to cause crystal transition; or not to desorb water of crystallization when the compound is a hydrate. Furthermore, even when the compound has such a stability (storage stability), a solvent that is used for obtaining the compound is required to be safe. However, as for the compound represented by Formula (I), no compounds satisfying such properties have been disclosed.

DISCLOSURE OF THE INVENTION

Problems to be Solved by the Invention

An object of the present invention is to provide a compound having properties usable for a pharmaceutical bulk powder for manufacturing pharmaceutical solid preparations with regard to the compound represented by Formula (I).

Means for Solving the Problems

The inventors of the present invention have found that: a hemihydrate of the compound represented by Formula (I) (which may be simply abbreviated as "hemihydrate" in the present specification; see, the following formula),

[Formula 2]

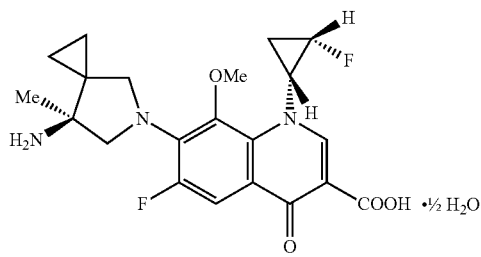

has a sufficient preservation stability; the hemihydrate can be prepared with a solvent having an excellent safety; and the hemihydrate has properties required to a pharmaceutical bulk powder. Thus the inventors have accomplished the present invention.

That is, the present invention relates to a hemihydrate of the compound represented by Formula (I).

[Formula 3]

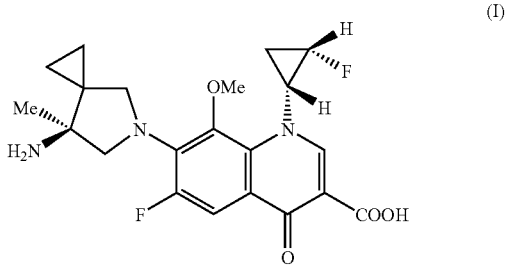

(I)

More specifically, the present invention relates to a compound represented by the following aspects:

1. 7-[(7S)-7-amino-7-methyl-5-azaspiro[2.4]heptan-5-yl]-6-fluoro-1-[(1R,2S)-2-fluorocyclopropyl]-8-methoxy-1,4-dihydro-4-oxoquinoline-3-carboxylic acid hemihydrate; and
2. the following formula

[Formula 4]

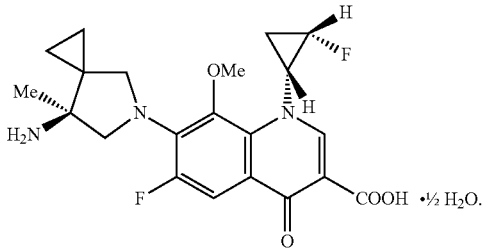

In addition, the present invention relates to a medicament comprising the hemihydrate.

Furthermore, the present invention relates to a pharmaceutical composition comprising the hemihydrate and a pharmaceutically acceptable carrier.

The present invention also relates to use of the hemihydrate for the manufacture of a medicament.

Moreover, the present invention relates to a method for preventing or treating infectious diseases wherein an effective amount of the hemihydrate is administered.

Advantageous Effect of the Invention

The present invention provides a compound that is stable and easily prepared. The present invention provides a compound that has excellent properties for a pharmaceutical bulk powder.

DETAILED DESCRIPTION OF THE PREFERRED EMBODIMENTS

Figure 1:
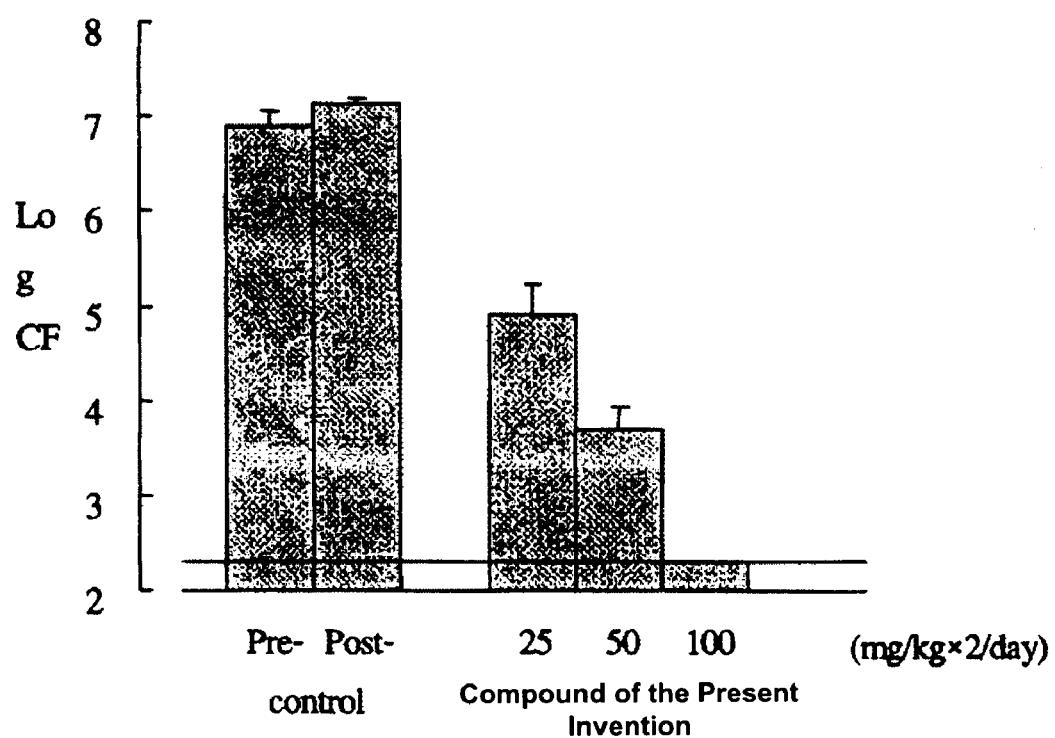
FIG. 1 is a diagram showing therapeutic efficacy of the hemihydrate of the compound represented by Formula (I) in a murine lung PRSP local infection model.

The compound represented by Formula (I) can be manufactured, for example, according to Reference Examples 1 to 11 or Reference Examples 12 to 22, which are described later. That is, according to Reference Examples 1 to 11, the compound represented by Formula (I) can be manufactured in accordance with the following reaction formulae.

[Formula 5]

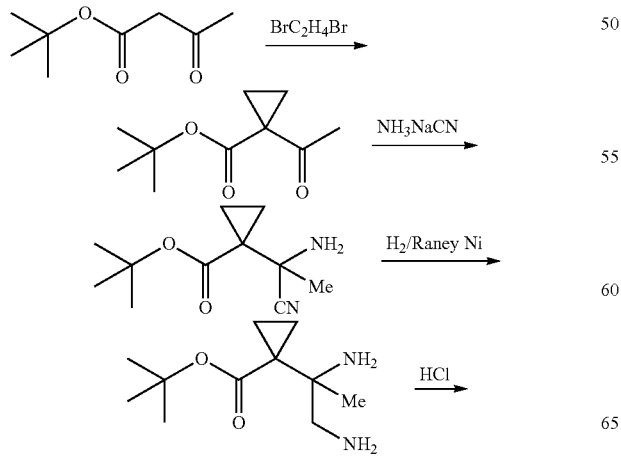

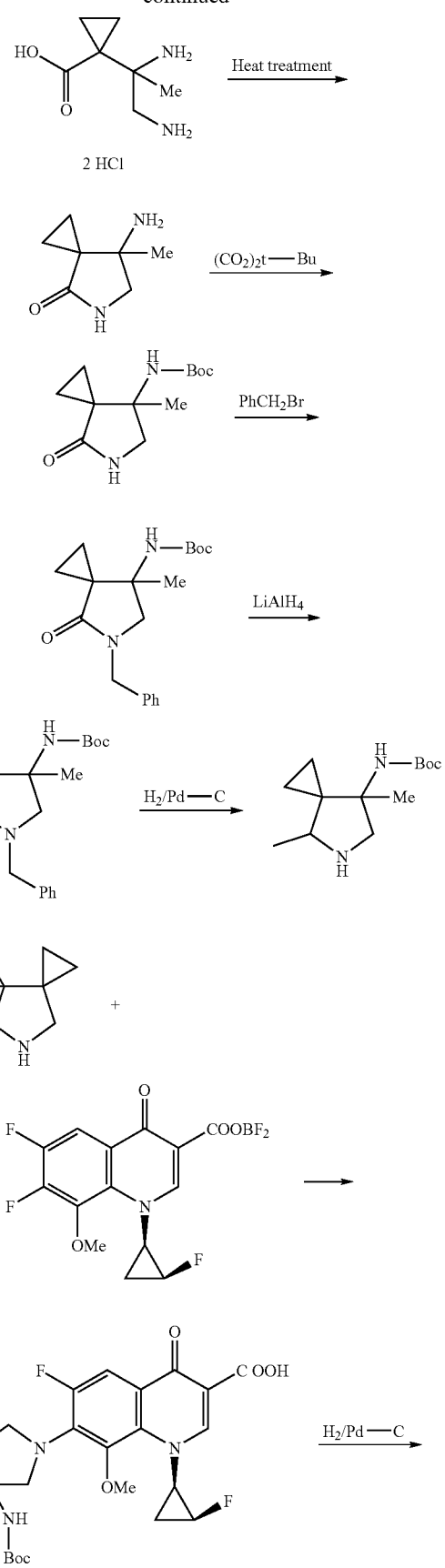

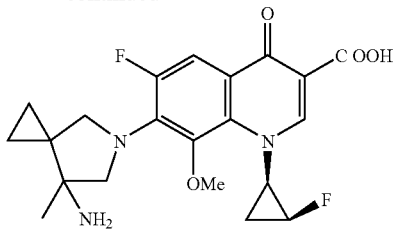

In addition, according to Reference Examples 12 to 22, the compound represented by Formula (I) can be manufactured in accordance with the following reaction formula.

[Formula 6]

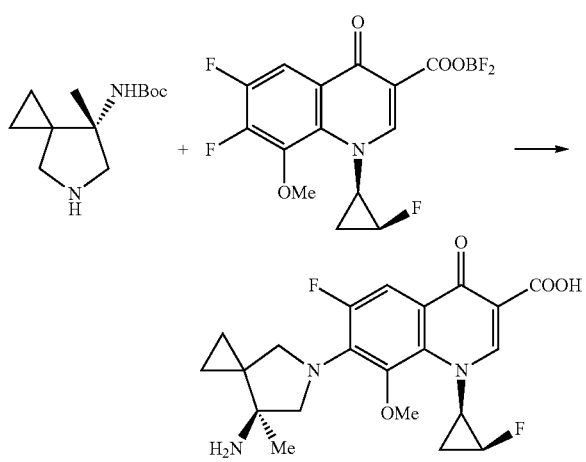

The hemihydrate according to the present invention can be obtained by recrystallizing the compound represented by Formula (I) from acetonitrile. For preparing the hemihydrate, various forms of the compound represented by Formula (I) may be used. Examples of such a compound may include anhydrides, ethanolate obtained in Reference Examples, and crude compounds of the hemihydrate itself.

An amount of acetonitrile to be used in the recrystallization of the hemihydrate from acetonitrile may be about 5 to 20 (v/w), preferably 5 to 15 (v/w) to the starting material. The recrystallization may be conducted in accordance with ordinary procedures in the art. In a preferred example, the material is added to acetonitrile, dissolved by heating to 50° C., and cooled to 25° C. to precipitate hemihydrate crystal.

Solvents other than acetonitrile may also be used to obtain the hemihydrate according to the present invention. Examples of such solvents may include esters, ketones and ethers. Examples of esters may include ethyl formate and methyl acetate. Examples of ketones may include methylethyl ketone, methyl isopropyl ketone, 2-pentanone, and 3-pentanone. Examples of ethers may include tetrahydrofuran. Furthermore, the above solvents may be used as mixed solvents with alcohol or water. In the case of using such solvents, as is the case with using acetonitrile, the material is added to the solvents, dissolved by heating to 50° C., and cooled to 25° C. to precipitate hemihydrate crystal.

Surprisingly, it has been found that the hemihydrate according to the present invention has the following excellent properties:
1. The weight of such a compound changes slightly with humidity changes, namely the compound shows stable moisture sorption and desorption behavior;
2. For moisture sorption and desorption change after thermal dehydration, the compound is rehydrated rapidly after thermal dehydration, and the compound remains almost the same properties as before the thermal treatment;
3. For change of crystalline form after thermal dehydration, the compound has its crystalline state even after being dehydrated, and restores to a stable hemihydrate by moisture sorption, thus the compound is rehydrated rapidly;
4. The crystalline form the compound does not change during storage; and
5. The compound is stable and does not change in its content under wet thermal condition or dry thermal condition.

And also it has been found that the compound has an excellent stability and is preferable for a pharmaceutical bulk powder.

The hemihydrate according to the present invention exhibits strong antibacterial activity, and thus the hemihydrate can be used as a medicament for humans, animals, or fishes; an agricultural chemical; or a preservative for foods. In the case of using the hemihydrate according to the present invention as a medicament for humans, its daily dose for adults may be from 50 mg to 1 g, preferably from 100 to 500 mg. The dose for veterinary use varies depending on an object of administration, the size of an animal to be treated, the type of microorganisms that infects the animal, and the degree of symptoms, but in general the daily dose of 1 to 200 mg is preferable, particularly 5 to 100 mg, per 1 kg of body weight of the animal. The daily dose is administered once a day, or twice to four times a day. The daily dose may exceed the above-mentioned amount, if necessary.

The hemihydrate according to the present invention is active against a wide range of microorganisms that cause various types of infectious diseases, and the hemihydrate can treat, prevent or alleviate the diseases caused by such pathogenic microorganisms. Bacteria and bacteria-like microorganisms against which the compound according to the present invention is active may include: *Staphylococcus, Streptococcus pyogenes, Streptococcus haemolyticus, Enterococcus, Streptococcus pneumoniae, Peptostreptococcus, Gonococcus, Escherichia coli, Citrobacter, Shigella, Klebsiella pneumoniae, Enterobacter, Serratia, Proteus, Pseudomonas aeruginosa, Haemophilus influenzae, Acinetobacter, Campylobacter*, and *Chlamydia trachomatis*.

Examples of diseases caused by the pathogens mentioned above may include: folliculitis, furuncle, carbuncle, erysipelas, cellulitis, lymphangitis, lymphadenitis, whitlow, subcutaneous abscess, hidradenitis, acne conglobata, infectious atheroma, perirectal abscess, mastitis, superficial secondary infection such as trauma, thermal burn, or operative wound, laryngopharyngitis, acute bronchitis, tonsillitis, chronic bronchitis, bronchiectasia, diffuse panacinar bronchitis, secondary infection from chronic respiratory disease, pneumonia, pyelonephritis, cystitis, prostatitis, epididymitis, gonococcal urethritis, nongonococcal urethritis, cholecystitis, cholangitis, bacillary dysentery, enteritis, uterine adnexitis, intrauterine infection, bartholinitis, blepharitis, hordeolum, dacryocystitis, inflammation of tarsal glands, ulcer of cornea, otitis media, sinusitis, periodontitis, pericoronitis, jaw inflammation, peritonitis, endocarditis, sepsis, meningitis and skin infection.

Furthermore, examples of acid fast bacteria against which the compound according to the present invention is active may include: *Mycobacterium tuberculosis* complex such as *Mycobacterium tuberculosis, M. bovis* or *M. africanum*; atypical mycobacteria complex such as *M. kansasii, M. marinum, M. scrofulaceum, M. avium, M. intracellulare, M. xenopi, M. fortuitum*, or *M. chelonae*. Acid fast bacteria infectious diseases caused by these pathogens are mainly divided by offending bacteria into three groups: tuberculosis, atypical mycobacteria disease, and leprosy. *Mycobacterium tuberculosis* infectious diseases are observed in lung, further in thoracic cavity, trachea, bronchi, lymph node, systemic disseminated type, osteoarticular, meninges, brain, digestive organs such as bowel or liver, skin, mammary gland, eye, auris media, pharynx, urinary tract, male genital organs, female genital organs, and so on. Primary organ affected by atypical mycobacteria diseases (nontuberculous mycobacterial diseases) is lung, and also includes local lymphadenitis, skin soft tissue, osteoarticular, systemic disseminated type and so on.

Furthermore, the hemihydrate according to the present invention is active against various types of microorganisms that cause animal infectious diseases, for example, *Escherichia, Salmonella, Haemophilus, Bordetella, Staphylococcus, Mycoplasma*, and so on. Specific examples of the diseases may include: in aves, colibacillosis, pullorum disease, fowl paratyphoid, fowl cholera, infectious coryza, staphylococcosis, mycoplasma infection, and so on; in pigs, colibacillosis, salmonellosis, pasteurellosis, hemophilus infection, atrophic rhinitis, exudative epidermitis, mycoplasma infection, and so on; in bovines, colibacillosis, salmonellosis, hemorrhagic sepsis, mycoplasma infection, bovine contagious pleuropneumonia, mastitis, and so on; in canines, coliform sepsis, salmonellosis, hemorrhagic sepsisY, pyometra, cystitis, and so on; in felines, exudative pleurisy, cystitis, chronic rhinitis, hemophilus infection, diarrhea of kittens, mycoplasma infection, and so on.

As for an antibacterial agent containing the hemihydrate according to the present invention, proper pharmaceutical preparations may be selected depending on administration method, and prepared in accordance with commonly used preparation method for each pharmaceutical preparation. Examples of the dosage form of the antibacterial agent containing the hemihydrate according to the present invention as a main ingredient may include: tablet, powder, granule, capsule, solution, syrup, elixir, oily or aqueous suspension, and so on. For injection, a stabilization agent, an antiseptic agent, a solubilizing agent, and so on may be contained in preparation. Or a preparation to be prepared before using may be manufactured by containing a solution that may include these agents in a container and then processing the solution into solid preparations by freeze-drying and so on. Furthermore, one dose may be contained in the container, or multiple doses may be contained in the same container. Examples of an external preparation may include: solution, suspension, emulsion, ointment, gel, cream, lotion, spray, and so on.

Solid preparations may contain a pharmaceutically acceptable additive agent together with an active compound. Examples of the additive agent may include: fillers, binders, disintegrators, dissolution promoters, moistening agents, lubricants, and so on. Examples of liquid preparations may include solution, suspension, emulsion, and so on, and the liquid preparations may further contain suspending agents, emulsifying agents, and so on.

Examples of formulation for pharmaceutical preparations are shown below.

PREPARATION EXAMPLE 1

| [Capsule]: | |
|---|---|
| Hemihydrate | 100.0 mg |
| Corn Starch | 23.0 mg |

| -continued | |
|---|---|
| [Capsule]: | |
| Calcium Carboxymethylcellulose | 22.5 mg |
| Hydroxymethylcellulose | 3.0 mg |
| Magnesium Stearate | 1.5 mg |
| Total | 150.0 mg |

PREPARATION EXAMPLE 2

| [Solution]: | |
|---|---|
| Hemihydrate | 1 to 10 g |
| Acetic Acid or Sodium Hydroxide | 0.5 to 2 g |
| Ethyl p-Hydroxybenzoate | 0.1 g |
| Purified Water | 87.9 to 98.4 g |
| Total | 100 g |

PREPARATION EXAMPLE 3

| [Powder for mixing with animal feeding stuff]: | |
|---|---|
| Hemihydrate | 1 to 10 g |
| Corn Starch | 89.5 to 98.5 g |
| Light Anhydrous Silicic Acid | 0.5 g |
| Total | 100 g |

EXAMPLES

Hereinafter the present invention will be explained with Examples and Reference Examples. However, the present invention is not limited thereto.

Reference Example 1

Tert-butyl 1-acetyl-1-cyclopropanecarboxylate

[Formula 7]

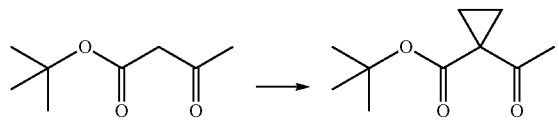

A mixture of tert-butyl acetoacetate (497 mL, 3.00 mol), 1,2-dibromoethane (310 mL, 3.60 mmol), potassium carbonate (1.106 kg, 8.00 mmol), and dimethylformamide (2.0 L) was heated and stirred in a water bath at 30° C. for 1.5 hours, in a water bath at 60° C. for 3.5 hours, and subsequently in a water bath at 30° C. for 4 days. The reaction solution was filtered through celite, and the residue was washed with diethyl ether (3.5 L). The filtrate and the diethyl ether washings were combined and added to water (2 L), to separate the organic layer. The aqueous layer was extracted with diethyl ether (2 L) and to the aqueous layer was added water (1 L). To thus obtained aqueous layer was further extracted with diethyl ether (2 L). The all organic layers were combined, and then washed with 10% aqueous solution of citric acid (2 L), water (2 L, 3 times), and saturated brine (2 L, 3 times). To this solution was added anhydrous sodium sulfate to dry the solution. The drying agent was removed by filtration, and the solvent was removed under reduced pressure. Thus obtained residue was distilled under reduced pressure, whereby 371.8 g of the target compound (fraction at 10 mmHg, and 72 to 78° C., 2.02 mol, 67%) was obtained as transparent and colorless oil.

$^1$H-NMR (400 MHz, CDCl$_3$) δppm: 1.37-1.40 (4H,m), 1.49 (9H,s), 2.44 (3H,s).

Reference Example 2

Tert-butyl 1-(1-amino-1-cyanoethyl)-1-cyclopropanecarboxylate

[Formula 8]

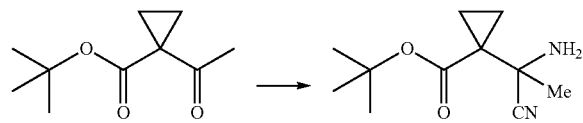

Tert-butyl 1-acetyl-1-cyclopropanecarboxylate (9.21 g, 50.0 mmol) was dissolved into a 7 N ammonia/methanol solution (300 mL). To this solution was added concentrated ammonia water (90 mL), ammonium chloride (53.5 g, 1.00 mmol), and sodium cyanide (4.90 g, 100.0 mmol) under cooling with ice, and subsequently the mixture was stirred at room temperature for 18 hours. The solvent was concentrated under reduced pressure. To the remaining solution was added water (100 mL), and subsequently extracted with dichloromethane (300 mL and 100 mL×2). To the combined organic layer was added anhydrous sodium sulfate to dry. The drying agent was removed by filtration, and the solvent was removed under reduced pressure to obtain 10.15 g of a crude product of the target compound (48.3 mmol, 97%) as light brown oil. The obtained crude product was used for the subsequent reaction without purifying further.

$^1$H-NMR (400 MHz, CDCl$_3$) δppm: 1.02-1.12 (2H,m), 1.19-1.17 (2H,m), 1.48 (9H,s), 1.50 (3H,s), 2.13 (2H,brs).

MS (ESI) m/z: 155 (M−tBu)$^+$.

Reference Example 3

Tert-butyl 1-(1,2-diamino-1-methylethyl)-1-cyclopropanecarboxylate

[Formula 9]

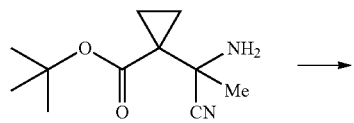

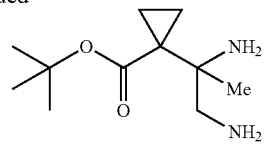

To an ethanol solution (50 mL) of tert-butyl 1-(1-amino-1-cyanoethyl)-1-cyclopropanecarboxylate (1.12 g, 5.30 mmol) was added an ethanol suspension (30 mL) of Raney Nickel catalyst (R-100 manufactured by NIKKO RICA CORPORATION, 10 mL), and the mixture was stirred vigorously under hydrogen atmosphere at room temperature for 6 hours. The catalyst was removed by filtration through celite, and the solvent was removed under reduced pressure to obtain 0.84 g of a crude product of the target compound (3.92 mmol, 74%) as transparent and colorless oil. The obtained crude product was used for the subsequent reaction without further purification.

$^1$H-NMR (trifluoroacetate, 400 MHz, DMSO-d$_6$) δppm: 1.08-1.19 (5H,m), 1.21-1.27 (1H,m), 1.28-1.33 (1H,m), 1.39 (9H,s), 3.27 (1H,d,J=12.9 Hz), 3.48 (1H,d,J=13.4 Hz), 8.34 (6H,brs).

MS (ESI) m/z: 215 (M+H)$^+$.

Reference Example 4

1-(1,2-Diamino-1-methylethyl)-1-cyclopropanecarboxylate dihydrochloride

[Formula 10]

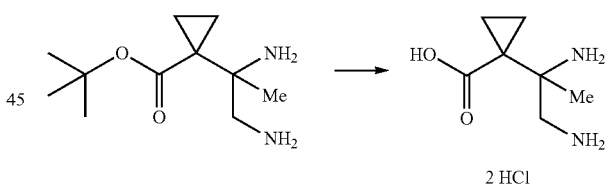

At room temperature, 0.82 g (3.83 mmol) of the crude product of tert-butyl 1-(1,2-diamino-1-methylethyl)-1-cyclopropanecarboxylate was dissolved in concentrated hydrochloric acid (5 mL), and the mixture was stirred at the same temperature for 30 minutes. To the reaction solution was added water, subsequently the solvent was removed under reduced pressure. And then the solution was subjected to azeotropy with ethanol (twice). As a result, 0.82 g of a crude product of the target compound (3.55 mmol, 930) was obtained as a light yellow foam-like solid. The obtained crude product was used for the subsequent reaction without further purification.

$^1$H-NMR (400 MHz, CD$_3$OD) δppm: 1.20-1.26 (1H,m), 1.28 (3H,s), 1.32-1.43 (2H,m), 1.58-1.62 (1H,m), 3.46 (1H, d,J=13.4 Hz), 3.80 (1H,d,J=13.4 Hz).

MS (ESI) m/z: 159 (M+H)$^+$.

Reference Example 5

7-(Tert-butoxycarbonylamino)-7-methyl-5-azaspiro[2.4]heptan-4-one

[Formula 11]

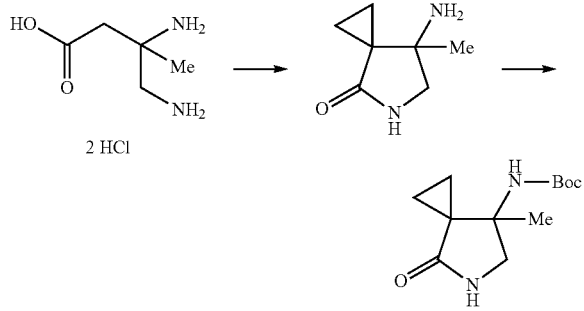

To an acetonitrile solution (70 mL) of the crude product (800 mg, 3.46 mmol) of 1-(1,2-diamino-1-methylethyl)-1-cyclopropanecarboxylate dihydrochloride was added 1,1,1,3,3,3-hexamethyldisilazane (7.38 mL, 34.6 mmol), and the mixture was heated under reflux under a nitrogen atmosphere in an oil bath at 100° C. for 4 hours. Then the solution was cooled to room temperature, and to the solution was added methanol (70 mL). After that, the solvent was removed under reduced pressure. Thus a crude product of 7-amino-7-methyl-5-azaspiro[2.4]heptan-4-one was obtained as a light brown gum-like solid.
MS (ESI) m/z: 141 (M+H)$^+$.

To thus-obtained crude product of 7-amino-7-methyl-5-azaspiro[2.4]heptan-4-one was added 1,4-dioxane (20 mL) and di-tert-butyl dicarbonate (1.528 g, 7.00 mmol) at room temperature. And this mixture was stirred at the same temperature for 5 hours. To this reaction mixture was added water (50 mL), and extracted with chloroform (100 mL and 50 mL). To the combined organic layer was added anhydrous sodium sulfate to dry. The drying agent was removed by filtration with a short silica gel column, and then the solvent was removed under reduced pressure. To thus-obtained residue was added diethyl ether to be suspend, and this suspension was filtered to obtain 502 mg (2.09 mmol, 2 steps, 60%) of the target compound as a white powder.
$^1$H-NMR (400 MHz, CDCl$_3$) δppm: 0.77-0.82 (1H,m), 0.94-1.04 (2H,m), 1.16-1.23 (1H,m), 1.28 (3H,s), 1.43 (9H,s), 3.29 (1H,d,J=10.3 Hz), 4.12 (1H,m), 4.60 (0.9H,brs), 5.82 (1H,brs).
MS (ESI) m/z: 185 (M−tBu)$^+$.

Reference Example 6

5-Benzyl-7-(tert-butoxycarbonylamino)-7-methyl-5-azaspiro[2.4]heptan-4-one

[Formula 12]

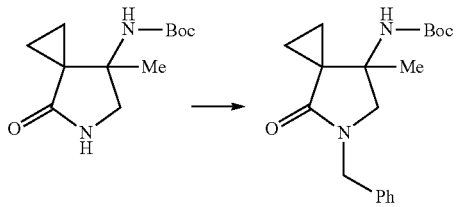

A dimethylformamide solution (65 mL) of 7-(tert-butoxycarbonylamino)-7-methyl-5-azaspiro[2.4]heptan-4-one (3.12 g, 12.97 mmol) was added sodium hydride (55%, mineral oil dispersion, 538 mg, 12.33 mmol) over 5 minutes under cooling with ice. This solution was stirred at the same temperature for 40 minutes. After that, to the solution was added benzyl bromide (1.851 mL, 15.56 mmol), and the mixture was stirred at room temperature for 1.5 hours. To this reaction mixture was added ethyl acetate (300 mL) to dilute the mixture, and the mixture was washed with water (100 mL, ×2) and saturated brine (100 mL). To the solution was added anhydrous sodium sulfate to dry the solution. The drying agent was removed by filtration, and then the solvent was removed under reduced pressure. Thus-obtained residue was purified with silica gel column chromatography (hexane/ethyl acetate in the ratio of and in the order of 9:1, 4:1, and 2:1) to obtain 4.20 g (12.71 mmol, 98%) of the target compound as a transparent and colorless gum-like solid.
$^1$H-NMR (400 MHz, CDCl$_3$) δppm: 0.76-0.81 (1H,m), 0.93-1.06 (2H,m), 1.21-1.29 (4H,m), 1.37 (9H,m), 3.14 (1H,d,J=10.3 Hz), 3.92-3.98 (1H,m), 4.44 (1H,d,J=15.1 Hz), 4.56 (1H,d,J=14.6 Hz), 4.56 (1H,brs), 7.22-7.33 (5H,m).
MS (ESI) m/z: 331 (M+H)$^+$.

Reference Example 7

(−)-5-Benzyl-7-(tert-butoxycarbonylamino)-7-methyl-5-azaspiro[2.4]heptan-4-one and (±)-5-benzyl-7-(tert-butoxycarbonylamino)-7-methyl-5-azaspiro[2.4]heptan-4-one The racemic mixture of 5-benzyl-7-(tert-butoxycarbonylamino)-7-methyl-5-azaspiro[2.4]heptan-4-one (2.254 g, 6.82 mmol) obtained in Reference Example 6 was subjected to optical resolution with an optically active column (CHIRALPAK AD, 20 mmφ×250 mm, hexane/isopropyl alcohol in the ratio of 90 to 10, flow rate=20 mL/minute, 50 mg was subjected to optical resolution per one time) to obtain (−)-5-benzyl-7-(tert-butoxycarbonylamino)-7-methyl-5-azaspiro[2.4]heptan-4-one (997 mg, 3.02 mmol, retention time=7.0 minutes, $[α]_D^{25.1}$=−113.9° (c=0.180, chloroform)); and (+)-5-benzyl-7-(tert-butoxycarbonylamino)-7-methyl-5-azaspiro[2.4]heptan-4-one (957 mg, 2.90 mmol, retention time=11.3 minutes, $[α]_D^{25.1}$=±108.8° (c=0.249, chloroform)).

Reference Example 8

(−)-5-Benzyl-7-(tert-butoxycarbonylamino)-7-methyl-5-azaspiro[2.4]heptane

[Formula 13]

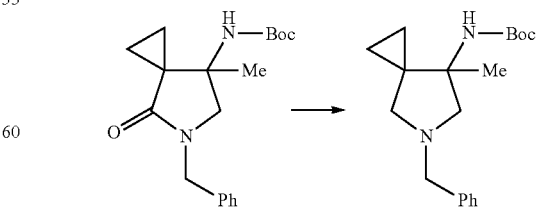

To a dichloromethane solution (15 mL) of the (−)-5-benzyl-7-(tert-butoxycarbonylamino)-7-methyl-5-azaspiro[2.4]heptan-4-one (950 mg, 2.88 mmol) was added trifluoroacetic acid (7.5 mL) at room temperature, and stirred at the same temperature for 40 minutes. The solvent was removed under reduced pressure, and the solution was subjected to azeotropy with toluene (twice). After that, to this solution was added a saturated aqueous solution (30 mL) of sodium bicarbonate, and the mixture was extracted with chloroform (100 mL and 50 mL×2). To the combined organic layer was added anhydrous sodium sulfate to dry the solution. The drying agent was removed by filtration, and then the solvent was removed under reduced pressure. Thus-obtained residue was dissolved in tetrahydrofuran (30 mL), to this solution was added lithium aluminum hydroxide (218 mg, 5.74 mmol) with stirring under cooling with ice, and the mixture was stirred at the same temperature for 1 hour. Furthermore, to this solution was added lithium aluminum hydroxide (109 mg, 2.87 mmol), and the mixture was stirred at room temperature for 2.5 hours. After that, this solution was cooled with ice and to this solution was cautiously added water (0.31 mL), 15% aqueous solution (0.31 mL) of sodium hydroxide and water (0.93 mL) sequentially. Thus-obtained mixture was stirred at room temperature overnight. And then to this mixture was added anhydrous sodium sulfate to dry the mixture, and the mixture was filtered through celite. The filtrate was concentrated under reduced pressure to obtain a crude product of 7-amino-5-benzyl-7-methyl-5-azaspiro[2.4]heptane as transparent and colorless oil. The obtained crude product was used for the subsequent reaction without further purification.

$^1$H-NMR (400 MHz, CDCl$_3$) δppm: 0.37-0.45 (2H,m), 0.56-0.66 (2H,m), 0.96 (3H,s), 2.48 (1H,d,J=9.0 Hz), 2.55 (1H,d,J=8.8 Hz), 2.74 (2H,d,J=9.0 Hz), 3.59 (2H,s), 7.21-7.37 (5H,m).

MS (ESI) m/z: 217 (M+H)$^+$.

Thus-obtained crude product of 7-amino-5-benzyl-7-methyl-5-azaspiro[2.4]heptane was dissolved in dichloromethane (15 mL), and to this solution was added di-tert-butyl dicarbonate (1.255 g, 5.75 mmol), and the solution was stirred at room temperature for 22 hours. Then the solvent was removed under reduced pressure. Thus-obtained residue was purified with silica gel column chromatography (chloroform/methanol/triethylamine in the ratio of 98:2:1 and then 95:5:1) to obtain 586 mg (1.852 mmol, 3 steps, 64%) of the target compound as a transparent and colorless gum-like solid.

$^1$H-NMR (400 MHz, CDCl$_3$) δppm: 0.40-0.45 (1H,m), 0.50-0.55 (1H,m), 0.63-0.69 (1H,m), 0.80-0.85 (1H,m), 1.20 (3H,s), 1.43 (9H,s), 2.44 (1H,d,J=8.8 Hz), 2.59 (1H,d,J=9.5 Hz), 2.83 (1H,d,J=8.8 Hz), 3.33 (1H,m), 3.57 (1H,d,J=13.2 Hz), 3.68 (1H,d,J=13.2 Hz), 4.75 (1H,brs), 7.20-7.37 (5H,m).

MS (ESI) m/z: 317 (M+H)$^+$.

$[α]_D^{25.1}$=−63.6° (c=0.129, chloroform)

Reference Example 9

(−)-7-(Tert-butoxycarbonylamino)-7-methyl-5-azaspiro[2.4]heptane

[Formula 14]

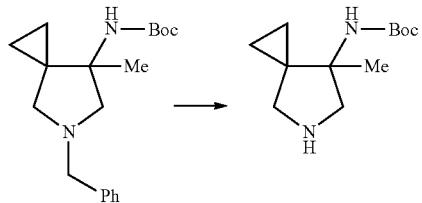

To a methanol solution (40 mL) of (−)-5-benzyl-7-(tert-butoxycarbonylamino)-7-methyl-5-azaspiro[2.4]heptane (581 mg, 1.836 mmol) was added 10% palladium carbon catalyst (M, water content of about 50%, 349 mg), and the mixture was stirred for 2.5 hours at room temperature under hydrogen atmosphere. The catalyst was removed by filtration, and the solvent was removed under reduced pressure. As a result, 434 mg (quantitative) of a crude product of the target compound was obtained as a transparent and colorless gum-like solid.

$^1$H-NMR (400 MHz, CDCl$_3$) δppm: 0.38-0.43 (1H,m), 0.55-0.60 (2H,m), 0.74-0.80 (1H,m), 1.08 (3H,s), 1.44 (9H,s), 2.75 (1H,d,J=12.0 Hz), 2.77 (1H,d,J=11.5 Hz), 3.13 (1H,d,J=11.5 Hz), 3.75 (1H,brd,J=12.0 Hz), 4.44 (1H,brs).

MS (ESI) m/z: 227 (M+H)$^+$.

$[α]_D^{25.1}$=−63.5° (c=0.277, chloroform)

Reference Example 10

7-[7-(Tert-butoxycarbonylamino)-7-methyl-5-azaspiro[2.4]heptan-5-yl]-6-fluoro-1-[(1R,2S)-2-fluorocyclopropyl]-8-methoxy-1,4-dihydro-4-oxoquinoline-3-carboxylic acid

[Formula 15]

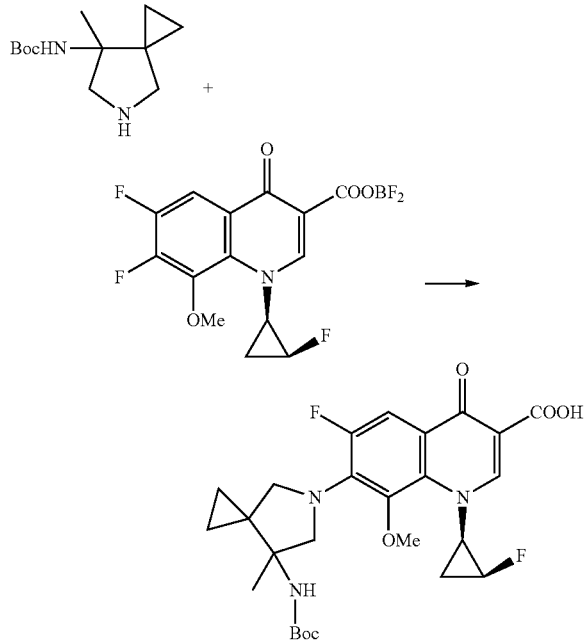

In dimethyl sulfoxide (5 mL) was dissolved the crude product of (−)-7-(tert-butoxycarbonylamino)-7-methyl-5-azaspiro[2.4]heptane (434 mg, 1.836 mmol) obtained in Reference Example 9; 6,7-difluoro-1-[(1R,2S)-2-fluorocyclopropyl]-8-methoxy-1,4-dihydro-4-oxoquinoline-3-carboxylic acid difluoroboron complex (663 mg, 1.836 mmol); and triethylamine (0.768 mL, 5.510 mmol). And this solution was heated and stirred in an oil bath at 40° C. for 14 hours. To this reaction solution was added a mixed solution (50 mL) of ethanol and water in the ratio of 4 to 1, and triethylamine (5 mL). And this solution was heated under reflux in an oil bath at 100° C. for 2 hours. The reaction solution was concentrated under reduced pressure. Thus-obtained residue was dissolved in ethyl acetate (200 mL) and washed with 10% aqueous solution of citric acid (50 mL), water (50 mL, ×2), and saturated brine (50 mL). The organic layer was dried over anhydrous sodium sulfate. Then the solvent was removed under reduced pressure to obtain 870 mg of a crude product of the target compound (1.676 mmol, 91%) as a yellow foam-like solid.

$^1$H-NMR (400 MHz, CDCl$_3$) δppm: 0.55-0.60 (1H,m), 0.68-0.73 (1H,m), 0.74-0.80 (1H,m), 0.92-0.97 (1H,m), 1.22 (3H,s), 1.40 (9H,s), 1.43-1.59 (2H,m), 3.13 (1H,d,J=9.8 Hz), 3.60 (3H,s), 3.75 (1H,dd,J=11.0, 3.7 Hz), 3.85 (1H,dt, J=10.2, 4.5 Hz), 4.18 (1H,d,J=10.0 Hz), 4.47 (1H,m), 4.62 (1H,s), 4.79-4.99 (1H,dm), 7.83 (1H,d,J=13.7 Hz), 8.68 (1H, d,J=2.7 Hz), 14.88 (0.7H,brs).

MS (ESI) m/z: 520 (M+H)$^+$.

$[α]_D^{25.1}$=−128.5° (c=1.240, chloroform)

Reference Example 11

7-(7-Amino-7-methyl-5-azaspiro[2.4]heptan-5-yl)-6-fluoro-1-[(1R,2S)-2-fluorocyclopropyl]-8-methoxy-1,4-dihydro-4-oxoquinoline-3-carboxylic acid

[Formula 16]

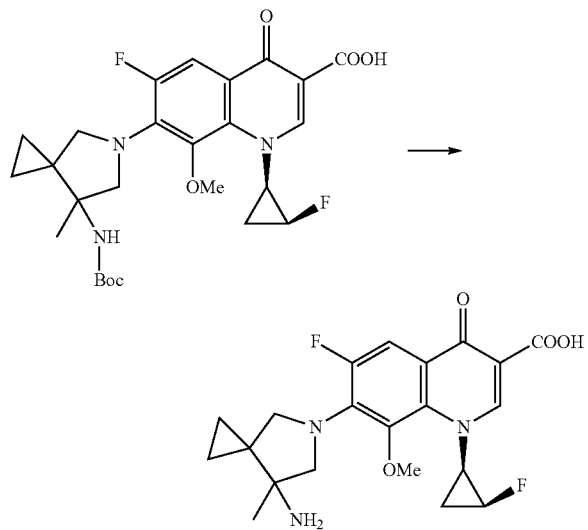

The 7-[7-(tert-butoxycarbonylamino)-7-methyl-5-azaspiro[2.4]heptan-5-yl]-6-fluoro-1-[(1R,2S)-2-fluorocyclopropyl]-8-methoxy-1,4-dihydro-4-oxoquinoline-3-carboxylic acid (870 mg, 1.676 mmol) obtained in Reference Example 10 was dissolved in concentrated hydrochloric acid (10 mL) under cooling with ice, the mixture was stirred at room temperature for 20 minutes, and this reaction solution was washed with chloroform (20 mL, ×5). To the aqueous layer was added a saturated aqueous solution of sodium hydroxide under cooling with ice, thereby making the solution to have pH 12.0. Subsequently, this solution was adjusted with hydrochloric acid to have pH 7.4. After that, the organic layer was extracted with a mixed solution of chloroform and methanol in the ratio of 10:1 (200 mL, ×2), and with an under layer of a solution of chloroform, methanol and water in the ratio of 7:3:1 (200 mL). The combined organic layer was dried over anhydrous sodium sulfate. Then the solvent was removed under reduced pressure. Thus obtained residue was purified by recrystallization from ethanol, dried under reduced pressure to obtain 644 mg (1.535 mmol, 92%) of the title compound as a light pink powder.

mp: 195-200° C.

$[α]_D^{25.1}$=+40.8° (c=0.147, 0.1N-NaOH).

$^1$H-NMR (400 MHz, 0.1N-NaOD) δppm: 0.49-0.56 (2H, m), 0.67-0.76 (2H,m), 1.12 (3H,s), 1.43-1.64 (2H,m), 3.56 (3H,s), 3.59-3.71 (4H,m), 3.99-4.04 (1H,m), 4.80-5.03 (1H, m), 7.65 (1H,d,J=13.9 Hz), 8.45 (1H,s).

Elemental Analysis for $C_{21}H_{23}F_2N_3O_4$·0.75EtOH·0.5H$_2$O;

Calculated Value: C, 58.37; H,6.20; F, 8.21; N, 9.08.

Actual Value: C, 58.23; H,5.99; F, 8.09; N, 9.02.

MS (EI) m/z: 419 (M$^+$).

IR (ATR): 2964, 2843, 1726, 1612, 1572, 1537, 1452, 1439, 1387, 1360, 1346, 1311, 1294, 1265, 1207 cm$^{-1}$.

Reference Example 12

Tert-butyl 5-oxo-1-[(1R)-1-phenylethyl]pyrrolidine-3-carboxylate

[Formula 17]

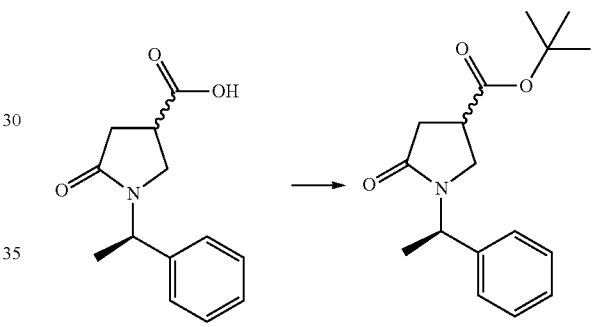

To a dichloromethane suspension (10 L) of 5-oxo-1-[(1R)-1-phenylethyl]pyrrolidine-3-carboxylic acid (1165 g, 4.994 mol) was added o-tert-butyl-N,N'-diisopropylurea (3020 g, 15.00 mol) at room temperature with being stirred with a blade. After increase of inner temperature and beginning of reflux were observed, the solution was cooled in an ice water bath. The reaction solution was cooled to room temperature, subsequently the ice water bath was removed and the solution was stirred for an hour, and then with heating the solution up to 40° C. for 3 hours. After that, this reaction solution was cooled in an ice water bath and stirred for an hour. Subsequently, an insoluble material was removed by filtration, and the filtrate was dried under reduced pressure. Thus obtained residue was purified with silica gel column chromatography (silica gel: 4 kg; eluant: hexane/ethyl acetate in the ratio of 3:1) to obtain 925.2 g (64%) of the title compound (mixture with 3-position isomer) as a light yellow syrup. Each diastereomer derived from 3-position of pyrrolidine was able to be fractionated easily; however, the compound was used without fractionating the diastereomers because the subsequent step is a reaction involving epimerization.

$^1$H-NMR spectrum of each isomer that was fractionated separately is shown below.

Low Polarity Isomer:

$^1$H-NMR (400 MHz, CDCl$_3$) δppm: 1.45 (9H,s), 1.54 (3H, d,J=7.08 Hz), 2.59-2.74 (2H,m), 2.95-3.03 (1H,m), 3.14 (1H, dd,J=9.77, 8.79 Hz), 3.49 (1H,dd,J=9.77, 6.35 Hz), 7.26-7.36 (5H,m).

High Polarity Isomer:
$^1$H-NMR (400 MHz, CDCl$_3$) δppm: 1.36 (9H,s), 1.53 (3H, d,J=7.32 Hz), 2.59-2.75 (2H,m), 3.02-3.11 (1H,m), 3.16 (1H, dd,J=10.01, 5.62 Hz), 3.51 (1H,dd,J=10.01, 8.54 Hz), 7.24-7.36 (5H,m).

Reference Example 13

Tert-butyl (3S)-3-methyl-5-oxo-1-[(1R)-1-phenyl-ethyl]pyrrolidine-3-carboxylate

[Formula 18]

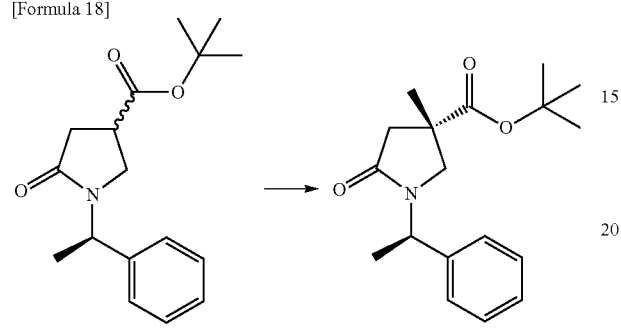

Under nitrogen atmosphere, to an N,N'-dimethylformamide solution (210 mL) of tert-butyl 5-oxo-1-[(1R)-1-phenylethyl]pyrrolidine-3-carboxylate (30.05 g, 0.104 mol) was added 26.0 mL of iodomethane (59.28 g, 0.418 mol), subsequently sodium hydride (550 oily, 11.35 g, 0.260 mol) with stirring the solution at room temperature. When inner temperature reached about 50° C., the solution was cooled to 30° C. in an ice water bath, then stirred for 23 hours in a water bath having an outside temperature of 17° C. This reaction solution was poured into a cold aqueous solution of citric acid (mixed water of 1 L of 10% citric acid and 500 g of ice water), stirred for 30 minutes, and then was extracted with ethyl acetate (800 mL and 500 mL). The organic layers were combined, washed with saturated brine, subsequently dried over anhydrous sodium sulfate, filtered, and the filtrate was dried under reduced pressure. Thus obtained residue was purified with flash silica gel column chromatography (hexane/ethyl acetate in the ratio of 5:1, and then 4:1 eluted parts) to obtain 10.63 g (33.7%) of the title compound as a white solid as a high polarity isomer: and 14.91 g (47.3%) of tert-butyl (3R)-3-methyl-5-oxo-1-[(1R)-1-phenylethyl]pyrrolidine-3-carboxylate a low polarity isomer.

$^1$H-NMR (400 MHz, CDCl$_3$) δppm: 1.34 (12H,s), 1.52 (3H,d,J=7.10 Hz), 2.27 (1H,d,J=17.0 Hz), 2.93 (1H,d,J=17.0 Hz), 3.05 (1H,d,J=10.1 Hz), 3.32 (1H,d,J=10.1 Hz), 5.50 (1H,q,J=7.1 Hz), 7.23-7.38 (5H,m).

Reference Example 14

Tert-butyl (3S)-4-[2-(tert-butyldimethylsilyl)hydroxyethyl]-3-methyl-5-oxo-1-[(1R)-1-phenyl-ethyl]pyrrolidine-3-carboxylate

[Formula 19]

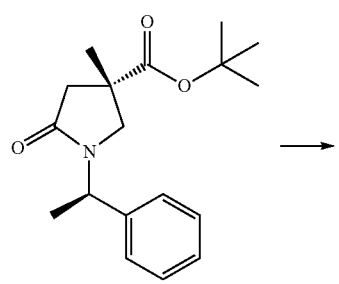

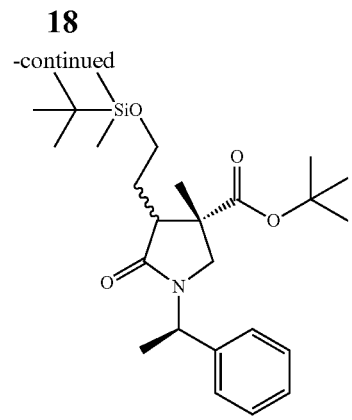

To an anhydrous tetrahydrofuran solution (288 mL) of (3S)-3-methyl-5-oxo-1-[(1R)-1-phenylethyl]pyrrolidine-3-carboxylate (30.0 g, 98.9 mmol) and tert-butyl (2-iodoethoxy)dimethylsilane (36.8 g, 129 mmol) was added dropwise lithium bis(trimethylsilyl) amide (1.0 M tetrahydrofuran solution, 129 mL, 129 mmol) at −4° C., and stirred at 2° C. for 3.5 hours. To this reaction solution was added a saturated solution (300 mL) of ammonium chloride, and the organic layer was extracted with ethyl acetate (300 mL, and 200 mL). The organic layer was washed with saturated brine (200 mL), subsequently dried over anhydrous sodium sulfate, filtered, and the filtrate was dried under reduced pressure to obtain 54.1 g of the title compound. Incidentally, this product was used in the subsequent step without purifying.
MS (ESI) m/z: 363 (M−Boc+H)$^+$.

Reference Example 15

Tert-butyl (3S)-4-(2-hydroxyethyl)-3-methyl-5-oxo-1-[(1R)-1-phenylethyl]pyrrolidine-3-carboxylate

[Formula 20]

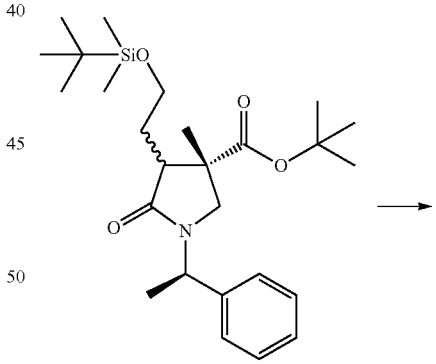

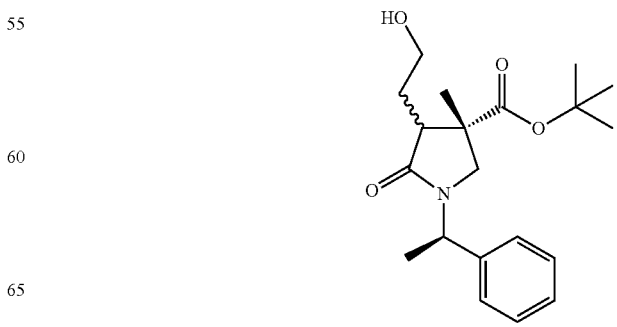

The above-mentioned crude product of silyl compound (54.1 g, 98.9 mmol) was dissolved in tetrahydrofuran (450 mL). To this solution was added dropwise a 1.0 mol/L tetrahydrofuran solution (148 mL, 148 mmol) of tetrabutylammonium fluoride under cooling with ice, and stirred for 2 hours at room temperature. The reaction solution was concentrated and the organic layer was extracted with ethyl acetate (200 mL, and 100 mL). The organic layer was washed with a 10% aqueous solution (200 mL) of sodium bicarbonate, an aqueous solution of citric acid (300 mL) and saturated brine (100 mL), subsequently dried over anhydrous sodium sulfate, filtered, and the filtrate was dried under reduced pressure. Thus obtained residue was purified with silica gel column chromatography (hexane/ethyl acetate in the ratio of and in the order of 6:1, 4:1, and 1:1 eluted parts) to obtain 29.1 g (83.9 mmol, 85%) of the title compound as a transparent and colorless syrup-like substance.

$^1$H-NMR (400 MHz, CDCl$_3$) δppm: 1.28 (3H,s), 1.40 (9H, s), 1.51-1.53 (1H,m), 1.53 (3H,d,J=7.1 Hz), 1.78-1.94 (2H, m), 2.90-3.08 (2H,m), 3.67-3.75 (1H,m), 3.80-3.91 (1H,m), 4.85-4.89 (1H,m), 5.43-5.53 (1H,m), 7.27-7.37 (5H,m).

MS (ESI) m/z: 348 (M+H)$^+$.

Reference Example 16

Tert-butyl (3S)-4-[2-(benzenesulfonyl)oxyethyl]-3-methyl-5-oxo-1-[(1R)-1-phenylethyl]pyrrolidine-3-carboxylate

[Formula 21]

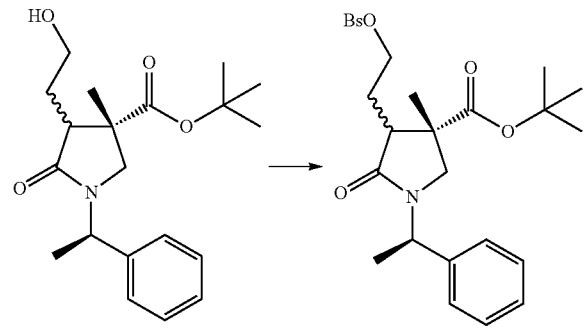

To a dichloromethane solution (280 mL) of tert-butyl (3S)-4-(2-hydroxyethyl)-3-methyl-5-oxo-1-[(1R)-phenylethyl]pyrrolidine-3-carboxylate (29.1 g, 83.9 mmol) was added triethylamine (15.2 mL, 109 mmol), benzenesulfonyl chloride (11.8 mL, 92.3 mmol), and 4-dimethylaminopyridine (1.02 g, 8.39 mmol) under cooling with ice. And this mixture was stirred at room temperature for 19 hours. To this reaction solution was added a saturated solution (280 mL) of ammonium chloride, and the organic layer was separated, and the solvent was removed therefrom under reduced pressure. Thus obtained residue was dissolved in ethyl acetate (280 mL and 180 mL), and washed again with the saturated solution of ammonium chloride. The organic layer was washed with a 1 mol/L aqueous solution (250 mL) of hydrochloric acid, a saturated aqueous solution (250 mL) of sodium bicarbonate, and saturated brine (200 mL). After that, the organic layer was dried over anhydrous sodium sulfate, filtered, and the filtrate was dried under reduced pressure to obtain a crude product of the benzene sulfonyl compound (43.7 g) in the title. This product was used in the subsequent step without purifying.

MS (ESI) m/z: 510 (M+Na)$^+$.

Reference Example 17

Tert-butyl (7S)-7-methyl-4-oxo-5-[(1R)-phenylethyl]-5-azaspiro[2.4]heptane-7-carboxylate

[Formula 22]

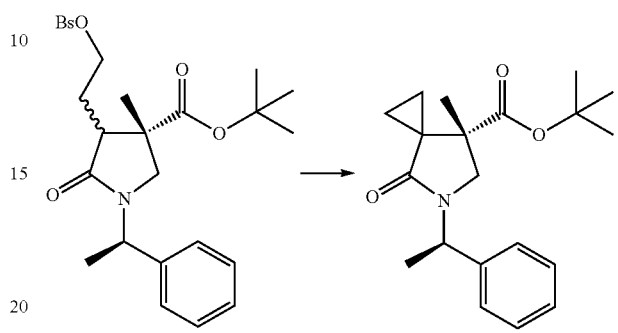

To an anhydrous tetrahydrofuran solution (470 mL) of the crude product of benzenesulfonyl compound (43.7 g, 83.9 mmol) was added a 1.0 mol/L tetrahydrofuran solution (109 mL, 109 mmol) of sodium bis(trimethylsilyl)amide under cooling with ice. And this mixture was stirred for at room temperature 1 hour. To this reaction solution was added a saturated solution (300 mL) of ammonium chloride, and the organic layer was extracted with ethyl acetate (300 mL and 200 mL). The organic layer was washed with saturated brine (200 mL), subsequently dried over anhydrous sodium sulfate, filtered, and the filtrate was dried under reduced pressure. Thus-obtained residue was purified with silica gel column chromatography (eluted with hexane/ethyl acetate in the ratio of 3:1 and then 2:1) to obtain 24.6 g (89%, 2 steps) of the title compound as a white solid.

mp: 55-57° C.

$[α]_D^{25.1}$=122.1° (c=0.517, CHCl$_3$).

$^1$H-NMR (400 MHz, CDCl$_3$) δppm: 0.72-0.77 (1H,m), 0.85-0.90 (1H,m), 1.04-1.13 (2H,m), 1.18 (3H,s), 1.32 (9H, s), 1.54 (3H,d,J=7.1 Hz), 3.08 (1H,d,J=9.8 Hz), 3.53 (1H,d, J=9.8 Hz), 5.52 (1H,q,J=7.1 Hz), 7.26-7.34 (5H,m).

Elemental Analysis for C$_{20}$H$_{27}$NO$_3$:

Calculated Value: C, 72.92; H,8.26; N, 4.25.

Actual Value: C, 72.64; H,8.27; N, 4.06.

MS (FAB) m/z: 330 (M+H)$^+$.

HRMS (FAB) m/z: 330.2069 (Calcd for C$_{20}$H$_{28}$NO$_3$ 330.2069).

IR (ATR) v: 3066, 2976, 2933, 2879, 1720, 1676, 1481, 1454, 1433, 1365, 1329, 1286, 1238, 1203 cm$^{-1}$.

For the compound, X-ray structural analysis was conducted for the purpose of determining the configuration at 7-position. After the data were collected, the initial phase was determined by the direct method, and the phase was determined precisely by the complete matrix least-squares method. When the phase was determined precisely, an anisotropic temperature factor was applied to non-hydrogen atoms, and hydrogen atoms were located by calculation to fix their coordinates. The compound has 2 asymmetric carbon atoms, and the absolute position of one of the carbon atoms was known. Based on the absolute position, an absolute position of another asymmetric carbon atom was determined. Thus, it was established that the configuration at 7-position of the title compound was (S), from which the configuration of a series of compounds prepared via the title compound was also determined.

Reference Example 18

(7S)-7-Methyl-4-oxo-5-[(1R)-phenylethyl]-5-azaspiro[2.4]heptane-7-carboxylic acid

[Formula 23]

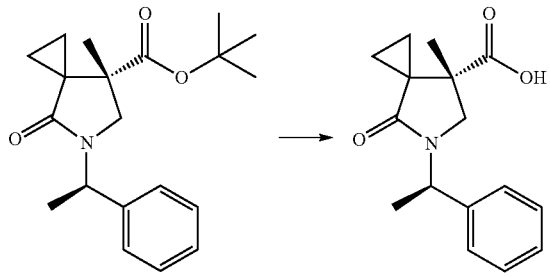

To a dichloromethane solution (120 mL) of the tert-butyl (7S)-7-methyl-4-oxo-5-[(1R)-phenylethyl]-5-azaspiro[2.4]heptane-7-carboxylate (24.5 g, 74.4 mmol) was added dropwise trifluoroacetic acid (120 mL) under cooling with ice, and the mixture was stirred for 2 hours. This reaction mixture was dried under reduced pressure. To thus-obtained residue was added toluene (20 mL), and dried under reduced pressure. Thus-obtained residue was dissolved in a 1 mol/L aqueous solution (300 mL) of sodium hydroxide under cooling with ice. This aqueous solution was washed with ethyl acetate (350 mL), and the solution was adjusted to pH 2 to 3 by adding concentrated hydrochloric acid (25 mL) to the aqueous layer under cooling with ice. And the organic layer was extracted with chloroform (300 mL×2).

The organic layer was washed with water (200 mL) and saturated brine (100 mL), subsequently dried over anhydrous sodium sulfate, and the solvent was removed under reduced pressure. To thus-obtained residue was added toluene (20 mL), and the mixture was dried under reduced pressure. Thus-obtained residue was suspended in chloroform (20 mL), hexane (200 mL) was added thereto, and subjected to crystallization. Precipitated solid was washed with hexane (100 mL) and dried under reduced pressure to obtain 20.48 g (quantitative) of the title compound as a white solid. This product was used in the subsequent step without purifying.

$^1$H-NMR (400 MHz, CDCl$_3$) δppm: 0.78-0.83 (1H,m), 0.90-0.95 (1H,m), 1.08-1.18 (2H,m), 1.24 (3H,s), 1.55 (3H,d,J=7.3 Hz), 3.11 (1H,d,J=10.0 Hz), 3.55 (1H,d,J=10.0 Hz), 5.52 (1H,q,J=7.1 Hz), 7.28-7.32 (5H,m).

MS (ESI) m/z: 274 (M+H)$^+$.

Reference Example 19

(7S)-7-Amino-7-methyl-4-oxo-5-[(1R)-phenylethyl]-5-azaspiro[2.4]heptane

[Formula 24]

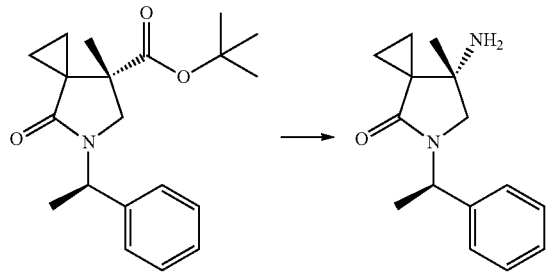

Triethylamine (20.7 mL, 149 mmol) was added to a toluene solution (200 mL) of (7S)-7-methyl-4-oxo-5-[(1R)-phenylethyl]-5-azaspiro[2.4]heptane-7-carboxylic acid (20.4 g, 74.4 mmol) and diphenyl phosphoric acid azide (17.6 mL, 81.8 mmol), and heated and stirred in an oil bath at 125° C. for 1 hour. This reaction solution was concentrated under reduced pressure to obtain a crude product of an isocyanate compound.

Thus-obtained isocyanate compound was dissolved in 1,4-dioxane (180 mL), and water (90 mL) and concentrated hydrochloric acid (90 mL) were added thereto. And this solution was heated and stirred in an oil bath at 50° C. for 1 hour. To this reaction solution was added water (200 mL), and the solution was washed with ethyl acetate (200 mL). And the solution was adjusted to have pH 9 to 10 by adding a 10 mol/L sodium hydroxide aqueous solution (170 mL) to the aqueous layer. And the organic layer was extracted with toluene (200 mL×2). The organic layer was washed with saturated brine (100 mL), dried over anhydrous sodium sulfate, filtered, and the filtrate was dried under reduced pressure to obtain 15.8 g (64.7 mmol) of the title compound as a light yellow oily material. This product was used in the subsequent step without purifying.

$^1$H-NMR (400 MHz, CDCl$_3$) δppm: 0.72-0.78 (2H,m), 0.99-1.10 (2H,m), 1.08 (3H,s), 1.53 (3H,d,J=7.4 Hz), 2.82 (1H,d,J=9.6 Hz), 3.27 (1H,d,J=9.6 Hz), 5.56 (1H,q,J=7.1 Hz), 7.14-7.37 (5H,m).

Reference Example 20

(7S)-7-(Tert-butoxycarbonylamino)-7-methyl-5-[(1R)-phenylethyl]-5-azaspiro[2.4]heptane

[Formula 25]

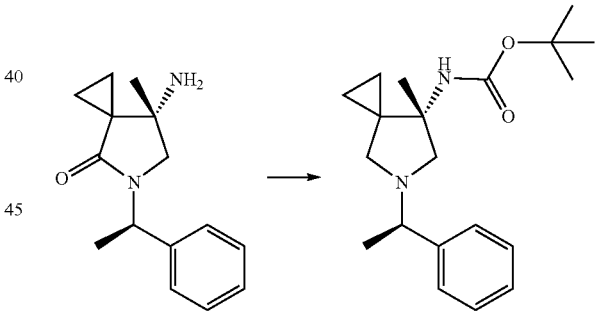

The (7S)-7-amino-7-methyl-4-oxo-5-[(1R)-phenylethyl]-5-azaspiro[2.4]heptane (15.8 g, 64.7 mmol) was dissolved in toluene (82 mL). While this solution was cooled with ice so that its inner temperature did not exceed 70° C., to this solution was added dropwise a toluene solution (6 mL) from a toluene solution (77.6 mL, 259 mmol) of 65% (by weight) solution of sodium bis(2-methoxyethoxy) aluminum hydride over 15 minutes. After that, the solution was heated and stirred in an oil bath at 80° C. for 10 minutes. This reaction solution was cooled with ice, and 25% (by weight) sodium hydroxide aqueous solution (158 mL) was added dropwise thereto to quench the reaction. And the organic layer was extracted with toluene (135 mL). The organic layer was washed with saturated brine (100 mL), and then di-tert-butyl dicarbonate (15.6 g, 71.2 mmol) was added thereto. The reaction solution was stirred at room temperature for 3 hours, and the solvent was removed under reduced pressure. Thus-obtained residue was purified with silica gel column chromatography (eluted with hexane/ethyl acetate in the ratio of and in the order of 8:1, 4:1, and 1:1) to obtain 18.0 g (73%) of the title compound as a transparent and colorless syrup-like substance.

$^1$H-NMR (400 MHz, CDCl$_3$) δppm: 0.37-0.49 (2H,m), 0.62-0.68 (1H,m), 0.77-0.82 (1H,m), 1.20 (3H,s), 1.32 (3H,d,J=6.6 Hz), 1.44 (9H,s), 2.46 (2H,dd,J=33.2, 9.3 Hz), 2.68 (1H,d,J=8.8 Hz), 3.27 (1H,q,J=6.6 Hz), 3.31-3.34 (1H,m), 4.71 (1H,s), 7.19-7.34 (5H,m).

MS (ESI) m/z: 331 (M+H)$^+$.

Reference Example 21

(7S)-7-(Tert-butoxycarbonylamino)-7-methyl-5-azaspiro[2.4]heptane

[Formula 26]

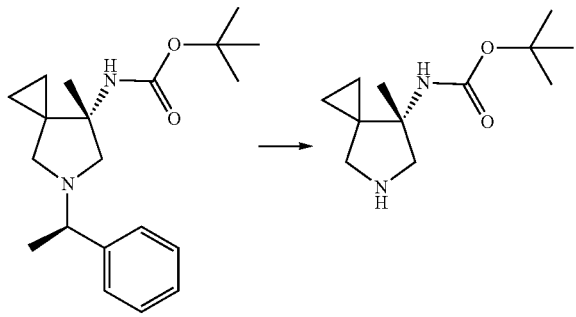

To a methanol solution (180 mL) of (7S)-7-(tert-butoxycarbonylamino)-7-methyl-5-[(1R)-phenylethyl]-5-azaspiro[2.4]heptane (18.0 g, 54.5 mmol) was added 10% palladium carbon catalyst (water content of 52.8%, 9.00 g). And this solution was stirred at room temperature under hydrogen atmosphere for 18 hours and furthermore stirred for 5.5 hours in an oil bath at 40° C. The catalyst was removed by filtration, and the solvent was dried under reduced pressure to obtain 13.4 g (quantitative) of a crude product of the title compound as a white solid.

$^1$H-NMR (400 MHz, CDCl$_3$) δppm: 0.38-0.43 (1H,m), 0.54-0.61 (2H,m), 0.74-0.80 (1H,m), 1.08 (3H,s), 1.44 (9H,s), 2.75 (1H,d,J=7.6 Hz), 2.78 (1H,d,J=7.1 Hz), 3.13 (1H,d,J=11.5 Hz), 3.73-3.77 (1H,m), 4.45 (1H,s).

MS (ESI) m/z: 227 (M+H)$^+$.

Reference Example 22

7-[(7S)-7-Amino-7-methyl-5-azaspiro[2.4]heptan-5-yl-6-fluoro-1-[(1R,2S)-2-fluorocyclopropyl]-8-methoxy-1,4-dihydro-4-oxoquinoline-3-carboxylic acid

[Formula 27]

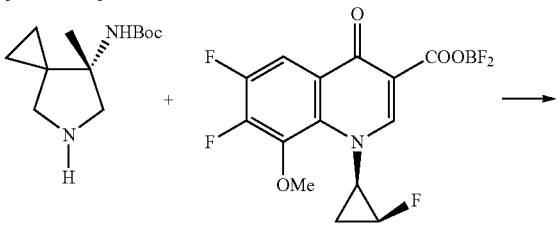

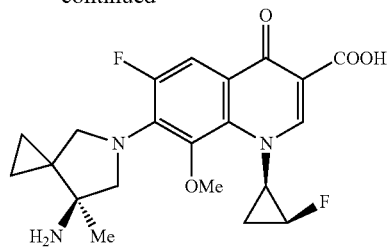

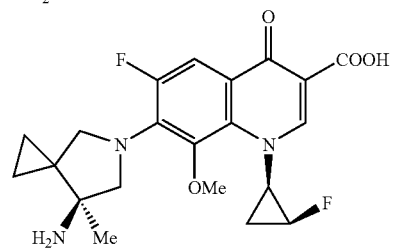

In dimethyl sulfoxide (52 mL) was dissolved (7S)-7-(tert-butoxycarbonylamino)-7-methyl-5-azaspiro[2.4]heptane (13.4 g, 54.5 mmol); 6,7-difluoro-1-[(1R,2S)-2-fluorocyclopropyl]-8-methoxy-1,4-dihydro-4-oxoquinoline-3-carboxylic acid-difluoro borane complex (17.9 g, 49.5 mmol); and triethylamine (8.97 mL, 64.4 mmol). And this solution was heated and stirred in an oil bath at 40° C. for 17 hours. This reaction solution was poured into cold water (1000 mL), and precipitated solid was filtered. To this solid was added a mixed solution (180 mL) of ethanol and water in the ratio of 5 to 1, and triethylamine (15 mL); and this solution was heated under reflux for 1.5 hours. The reaction mixture was dried under reduced pressure and thus-obtained residue was dissolved in ethyl acetate (150 mL×2), and washed with 10% citric acid aqueous solution (200 mL), water (200 mL), and saturated brine (100 mL). The organic layer was dried over anhydrous sodium sulfate. Then the solvent was removed under reduced pressure, and thus-obtained residue was dissolved in a mixed solution (100 mL) of chloroform and methanol in the ratio of 9 to 1, silica gel (10 g) was added thereto, and stirred for 1 hour. The silica gel was removed by filtration, and the solution was washed with a mixed solution (50 mL×2) of chloroform and methanol in the ratio of 9 to 1. The filtrate was combined, concentrated and dried. This residue was dissolved in concentrated hydrochloric acid (200 mL) under cooling with ice, subsequently stirred for 30 minutes at room temperature, and the reaction solution was washed with chloroform (400 mL×5). To the aqueous layer was added a 10 mol/L aqueous solution of sodium hydroxide under cooling with ice, thereby making the solution to have pH 11.8. Subsequently, this solution was adjusted with hydrochloric acid to have pH 7.4. After that, the organic layer was extracted with chloroform (100 mL×3). The organic layer was dried over anhydrous sodium sulfate. Then the solvent was removed under reduced pressure. Thus obtained residue was purified by recrystallization from ethanol, dried under reduced pressure to obtain 18.5 g (79%) of the title compound as a light pink powder.

Data of this product obtained with devices such as $^1$H-NMR were perfectly identical to data of the compound of Reference Example 11. That is, it was established that, in quinolone derivatives having a 7-amino-7-methyl-5-azaspiro[2.4]heptan-5-yl group, the quinolone derivative mentioned in Reference Example 11, which shows high activity, has steric configuration of (7S) at 7-position of the 5-azaspiro[2.4]heptan-5-yl group.

Test Example 1

Antibacterial activity of the hemihydrate of the compound represented by Formula (I) was measured in accordance with standard procedures designated by Japanese Society of Chemotherapy, and obtained results are shown by MIC (µg/mL) in Table 1. Among the strains in Table 1, *S. aureus,* 87037 and *S. pneumoniae,*J24 are resistant to quinolone. MIC values for levofloxacin (LVFX), gatifloxacin (GTFX), and ciprofloxacin (CPFX) are also shown in Table 1.

TABLE 1

|  | Hemihydrate | LVFX | GTFX | CPFX |
|---|---|---|---|---|
| *E. coli* NIHJ | 0.025 | 0.012 | 0.006 | ≦0.003 |
| *P. vulgaris,* 08601 | 0.025 | 0.012 | 0.006 | ≦0.003 |
| *S. marscecens,* 10100 | 0.1 | 0.1 | 0.1 | 0.025 |
| *P. aeruginosa,* 32104 | 0.39 | 0.2 | 0.2 | 0.05 |
| *P. aeruginosa,* 32121 | 0.2 | 0.1 | 0.1 | 0.025 |
| *S. aureus,* 209P | 0.025 | 0.2 | 0.05 | 0.1 |
| *S. epidermidis,* 56500 | 0.1 | 0.39 | 0.2 | 0.2 |
| *E. faecalis,* ATCC 19433 | 0.2 | 0.78 | 0.39 | 0.78 |
| *S. aureus,* 87037 | 0.78 | >6.25 | 1.56 | >6.25 |
| *S. pneumoniae,* J24 | 0.1 | 0.78 | 0.2 | 0.39 |
| MIC (µg/ml) | | | | |

Furthermore, anti-*mycobacterium tuberculosis* activity of the hemihydrate of the compound represented by Formula (I) was measured in accordance with standard procedures designated by Japanese Society of Chemotherapy (Japanese journal of Chemotherapy, vol. 29, page 76 to 79, 1981). Obtained results are shown by MIC (µg/mL). Activities against sensitive bacteria are shown in Table 2, and Activity against bacteria resistant to quinolone are shown in Table 3. RFP represents rifampicin. The hemihydrate of the compound represented by Formula (I) exhibited excellent antibacterial activity against *Mycobacterium tuberculosis*.

TABLE 2

| Strain/Compound | Compound of the Present Invention | RFP |
|---|---|---|
| TB-s 2 | 0.06 | 0.03 |
| TB-s 3 | 0.06 | 0.125 |
| TB-s 4 | 0.06 | 0.06 |
| TB-s 5 | 0.06 | 0.06 |
| TB-s 6 | 0.06 | 0.125 |
| TB-s 7 | 0.06 | 0.06 |
| TB-s 8 | 0.03 | 0.015 |
| TB-s 9 | 0.06 | 0.06 |
| TB-s 10 | 0.03 | 0.06 |
| TB-s 11 | 0.06 | 0.06 |
| TB-s 12 | 0.125 | 0.125 |
| TB-s 13 | 0.06 | 0.06 |
| TB-s 14 | 0.06 | 0.03 |
| TB-s 15 | 0.06 | 0.06 |
| TB-s 16 | 0.06 | 0.06 |
| TB-s 17 | 0.06 | 0.06 |
| TB-s 18 | 0.06 | 0.03 |
| TB-s 19 | 0.06 | 0.125 |
| TB-s 20 | 0.06 | 0.25 |
| TB-s 21 | 0.06 | 0.03 |
| TB-s 22 | 0.03 | 0.015 |
| Kurono | 0.03 | 0.06 |
| H37Rv | 0.03 | 0.125 |
| Ravenel | 0.03 | 0.125 |

TABLE 3

| Strain/Compound | Compound of the Present Invention | RFP |
|---|---|---|
| s 1 | 1 | 16 |
| MDR 1 | 0.125 | 16 |
| MDR 3 | 0.125 | 128 |
| MDR 4 | 0.25 | 64 |
| MDR 5 | 0.5 | 32 |
| MDR 7 | 0.125 | >128 |
| MDR 9 | 0.125 | 128 |
| MDR 12 | 0.125 | 128 |
| 1 (QR-3) | 0.125 | >128 |
| 2 (QR-6) | 0.5 | >128 |
| 3 (QR-1) | 0.25 | 128 |
| 4 (QR-9) | 0.25 | >128 |

Test Example 2

Therapeutic Efficacy in Murine Lung Local Infection Model

Therapeutic efficacy of the hemihydrate of the compound represented by Formula (I) was examined in murine lung local infection model infected by penicillin-resistant *streptococcus pneumonia* (PRSP), by administering the hemihydrate orally to the model.

PRSP 033806 strain anaerobically cultured with TODD-HEWITT BROTH was inoculated by nasal drip into male CBA/JNCrlj mice (3 to 4 weeks old, from CHARLES RIVER LABORATORIES JAPAN, INC., 4 mice in a group) anesthetized with ketamine/xylazine. To the infection model was orally administered the hemihydrate of the compound represented by Formula (I) at doses shown in Table 2 (25, 50 and 100 mg/kg/day) at 2 hours and 8 hours after infection (one day therapy, 50, 100, and 200 mg/kg/day as a daily dose). To a untreated control group, distilled water for injection was administered.

Bacterial count in the lung was measured in the control group just before administering the medicament (2 hours after infection, pre-control), the control group on the next day of administering the medicament (the next day of infection, post-control), and the medicament administered group, and used as indicator of therapeutic efficacy.

Test Example 3

Therapeutic Efficacy in Rat Simple Cystitis Model (*E. Coli*)

Infected Model: rats (Crl: CD (SD) (IGS), female, 7 weeks old, from CHARLES RIVER LABORATORIES JAPAN, INC., 4 rats in a group) without having water from the previous day were anesthetized with ketamine/xylazine, and then *E. coli* E77156 strain was inoculated transurethrally into the urinary bladder ($1.2 \times 10^7$ CFU/rat). After the inoculation, for the purpose of preventing excretion of the strain solution, the urethral opening was blocked for 2 hours. And immediately after releasing the blockage, water was provided again.

Administration of Agent: the hemihydrate of the compound represented by Formula (I) was orally administered once at a dose of 5, 20, and 80 mg/kg on the next day of infection.

Figure 2:
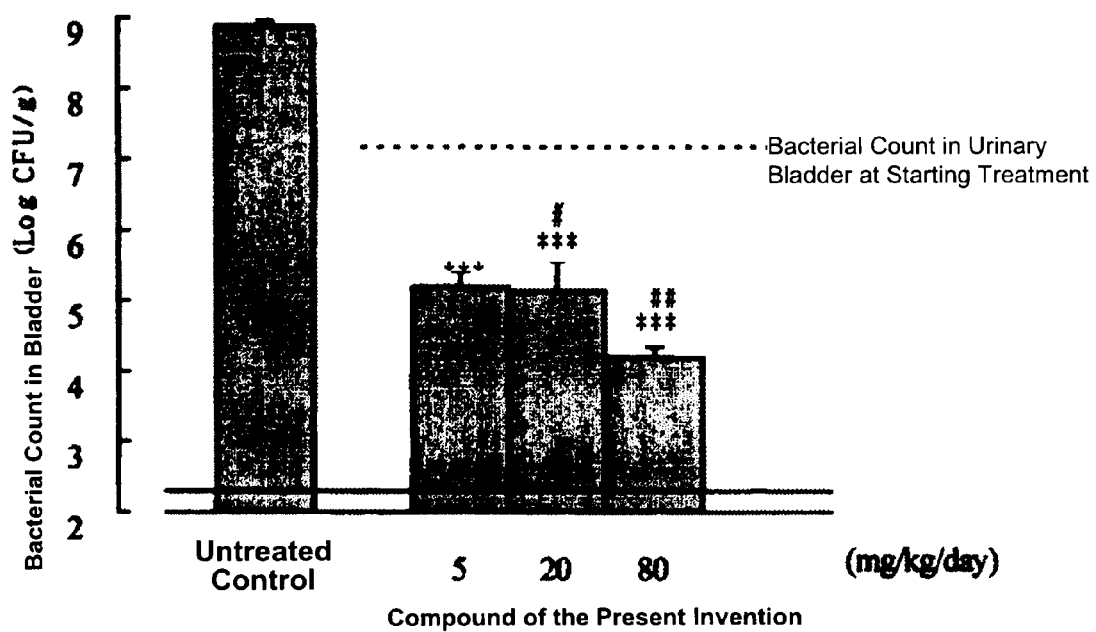
FIG. 2 is a diagram showing therapeutic efficacy of the hemihydrate of the compound represented by Formula (I) in a rat model of simple cystitis caused by *E. coli*.

Evaluation of Efficacy: Bacterial count in the bladder was measured in the control group and the medicament administered group just before administering the medicament, and the next day of administering the medicament (two days after infection). The measured values were used as indicator of therapeutic efficacy. Results: The hemihydrate of the compound represented by Formula (I) exhibited statistically significant decrease in bacterial count in comparison with the count at beginning of the treatment (FIG. 2). That is, together with the previous Test Examples, it has been demonstrated that the hemihydrate of the compound represented by Formula (I) is a compound that exhibits excellent therapeutic efficacy.

Example 1

Figure 3:
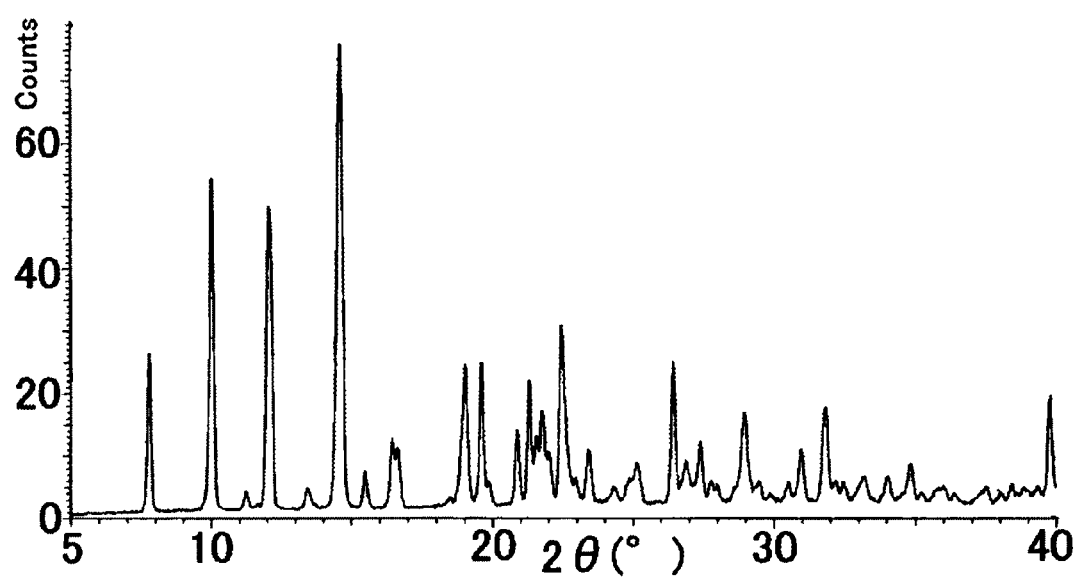
FIG. 3 is a diagram showing a powder X-ray diffraction spectrum of the compound according to the present invention: 7-[(7S)-7-amino-7-methyl-5-azaspiro[2.4]heptan-5-yl]-6-fluoro-1-[(1R,2S)-2-fluorocyclopropyl]-8-methoxy-1,4-dihydro-4-oxoquinoline-3-carboxylic acid hemihydrate.
Figure 4:
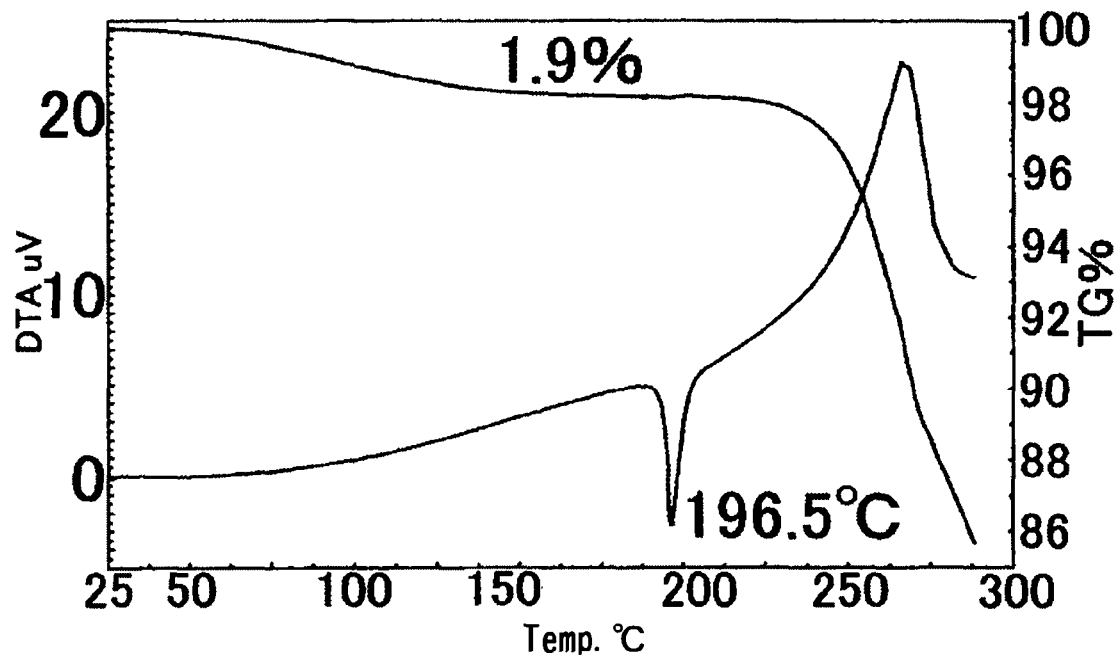
FIG. 4 is a diagram showing a thermal analysis (TG/DTA) spectrum of the compound according to the present invention.

7-[(7S)-7-Amino-7-methyl-5-azaspiro[2.4]heptan-5-yl]-6-fluoro-1-[(1R,2S)-2-fluorocyclopropyl]-8-methoxy-1,4-dihydro-4-oxoquinoline-3-carboxylic acid hemihydrate Acetonitrile (16 mL) was added to 7-[(7S)-7-amino-7-methyl-5-azaspiro[2.4]heptan-5-yl]-6-fluoro-1-[(1R,2S)-2-fluorocyclopropyl]-8-methoxy-1,4-dihydro-4-oxoquinoline-3-carboxylic acid (2.08 g); and heated to about 50° C. to dissolve it. This solution was cooled to room temperature and then stirred for one day to precipitate crystal. Precipitated crystals were filtered and air-dried to obtain 1.19 g (57%) of hemihydrate, which was the title compound. This crystal was measured by powder X-ray diffraction (FIG. 3), thermal analysis (TG/DTA) (FIG. 4), and elemental analysis and confirmed as hemihydrate, that is, the title compound.
Elemental Analysis for $C_{21}H_{23}N_3O_4F_2 \cdot 1/2H_2O$
Calculated Value: C, 58.87; H,5.65; N, 9.81; F, 8.87.
Actual Value: C, 58.73; H,5.65; N, 9.94; F, 8.87.
The measurement condition of powder X-ray diffraction was as follows:
Device: X' Pert-MPD PW3050 from Philips
Scanning Speed: 0.015° 2θ/s
Scanning Range: 5 to 40°
The measurement condition of thermal analysis (TG/DTA) was as follows:
Thermal Analysis Device: SSC5200 TG/DTA220 from Seiko Instruments & Electronics Ltd.
Rate of Temperature Increase: 10° C./min
Atmosphere: nitrogen gas 200 mL/min Evaluation Example 1

Moisture Sorption and Desorption Behavior

Figure 5:
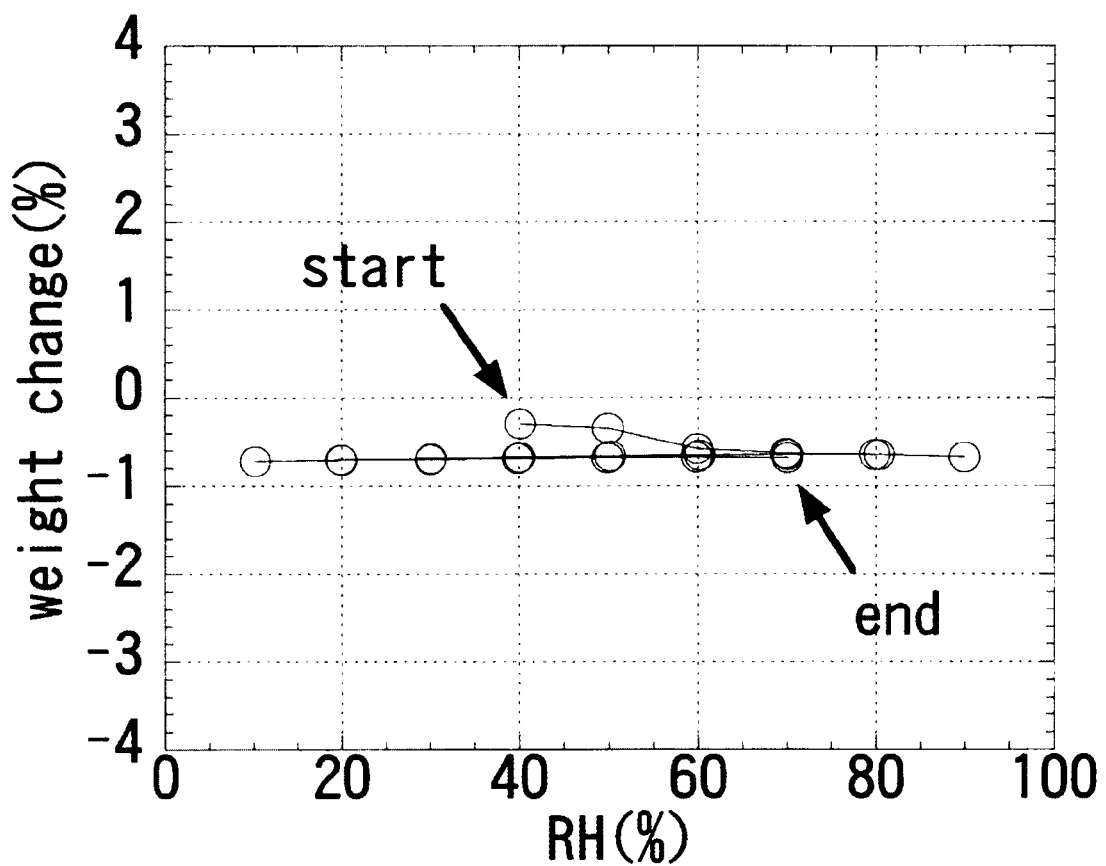
FIG. 5 is a diagram showing moisture sorption and desorption behavior pattern of the compound according to the present invention.

Moisture sorption and desorption behavior was examined with an atmospheric pressure type automatic water vapor adsorption device for 7-[(7S)-7-amino-7-methyl-5-azaspiro[2.4]heptan-5-yl]-6-fluoro-1-[(1R,2S)-2-fluorocyclopropyl]-8-methoxy-1,4-dihydro-4-oxoquinoline-3-carboxylic acid hemihydrate obtained in Example 1. Results are shown in FIG. 5. The weight change of this crystal was 1% or less as humidity changes, indicating that the crystal is stable.

Evaluation Example 2

Change in Moisture Sorption and Desorption after Thermal Dehydration

Figure 6:
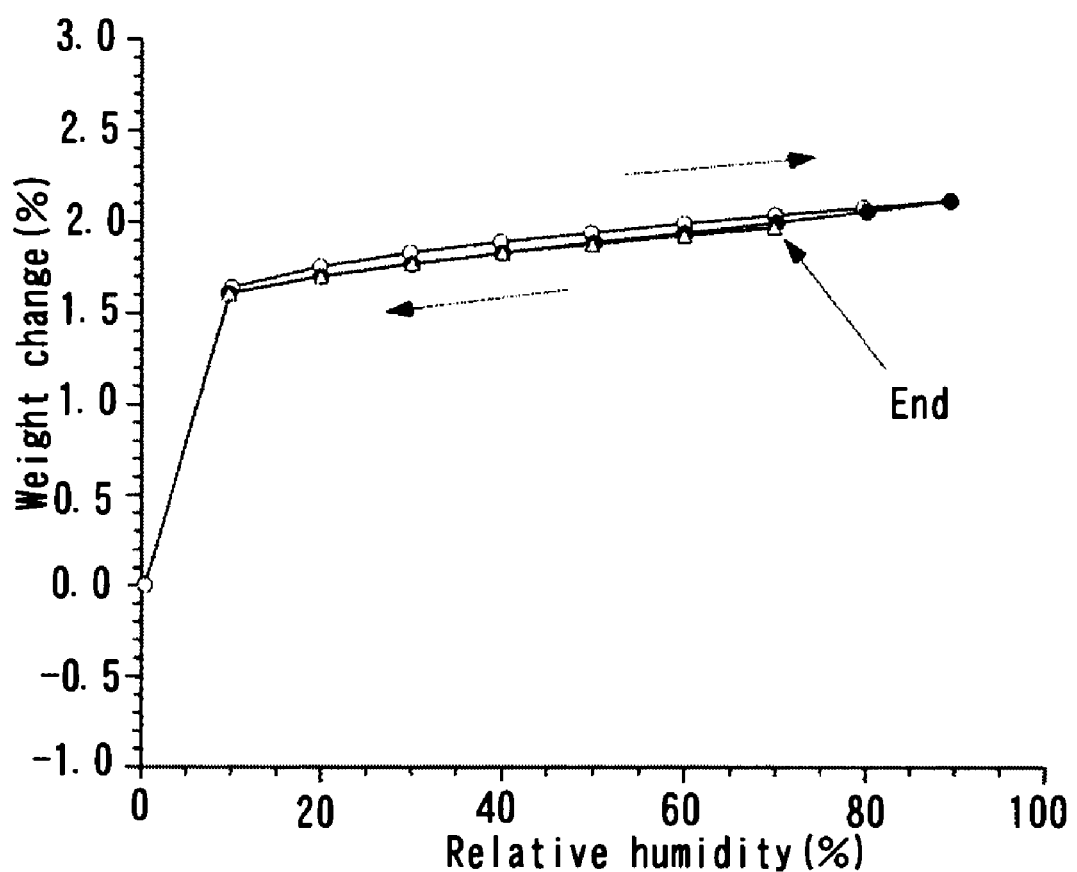
FIG. 6 is a diagram showing moisture sorption and desorption change pattern of the compound according to the present invention after thermal dehydration (60° C.)

Change in moisture sorption and desorption after thermal dehydration (60° C.) was examined for 7-[(7S)-7-amino-7-methyl-5-azaspiro[2.4]heptan-5-yl]-6-fluoro-1-[(1R,2S)-2-fluorocyclopropyl]-8-methoxy-1,4-dihydro-4-oxoquinoline-3-carboxylic acid hemihydrate obtained in Example 1. Results are shown in FIG. 6. The compound was rehydrated rapidly after being dehydrated, and moisture sorption and desorption behavior of the compound remained about the same as before the thermal treatment.

Evaluation Example 3

Change in Crystalline Form after Thermal Dehydration

Figure 7:
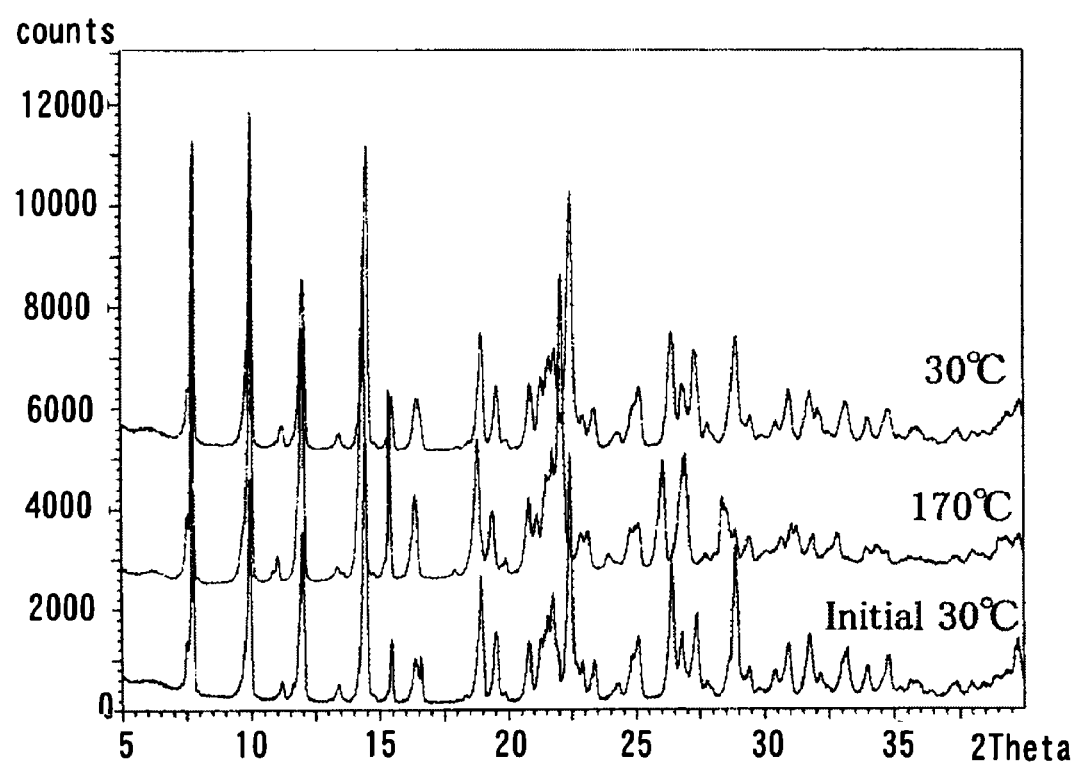
FIG. 7 is a diagram showing change patterns of X-ray diffraction spectra of the compound according to the present invention on thermal treatments.

Change in crystalline form by thermal treatment was examined for 7-[(7S)-7-amino-7-methyl-5-azaspiro[2.4]heptan-5-yl]-6-fluoro-1-[(1R,2S)-2-fluorocyclopropyl]-8-methoxy-1,4-dihydro-4-oxoquinoline-3-carboxylic acid hemihydrate obtained in Example 1.
Results are shown in FIG. 7. The compound had its crystalline state even after being dehydrated, and only a little difference was observed in its diffraction pattern, suggesting that the compound restores to stable hemihydrate after absorbing water and is rehydrated rapidly.

Evaluation Example 4

Crystal Stability

Weight change and crystalline form were examined as to 7-[(7S)-7-amino-7-methyl-5-azaspiro[2.4]heptan-5-yl-6-fluoro-1-[(1R,2S)-2-fluorocyclopropyl]-8-methoxy-1,4-dihydro-4-oxoquinoline-3-carboxylic acid hemihydrate obtained in Example 1 by being stored under the condition of 0, 52 or 93% of relative humidity, at 25° C. for 3 days. The crystalline form was evaluated by measuring with powder X-ray diffraction and thermal analysis. As results, the weight changed slightly (Table 4), and the crystalline form did not change.

TABLE 4

| Crystalline Stability of Hemihydrate [Weight Change (%)] | | |
|---|---|---|
| 0% RH | 52% RH | 93% RH |
| 0.00 | 0.43 | 0.61 |

Evaluation Example 5

Chemical Stability

7-[(7S)-7-amino-7-methyl-5-azaspiro[2.4]heptan-5-yl]-6-fluoro-1-[(1R,2S)-2-fluorocyclopropyl]-8-methoxy-1,4-dihydro-4-oxoquinoline-3-carboxylic acid hemihydrate obtained in Example 1 was each stored for 2 weeks under wet heat condition (40° C., 75% RH), dry heat condition (50° C., of 0% RH) and photo irradiation condition. Results are shown in Table 5. The compound according to the present invention was stable and its content was not decreased under the wet heat condition and the dry heat condition. However, under the photo irradiation condition, color change and some decrease in remaining ratio of the compound were observed.

TABLE 5

| Chemical Stability of Hemihydrate | | | | | |
|---|---|---|---|---|---|
| 40° C., 75% RH | | 50° C., 0% RH | | Photo (1x · hr) | |
| 1 week | 2 week | 1 week | 2 week | $6 \times 10^5$ | $1.2 \times 10^6$ |
| 99.4 | 100 | 101 | 101 | 97.0 | 95.1 |

[Remaining Weight Ratio (%)]

What is claimed is:

1. 7-[(7S)-7-amino-7-methyl-5-azaspiro[2.4]heptan-5-yl]-6-fluoro-1-[(1R,2S)-2-fluorocyclopropyl]-8-methoxy-1,4-dihydro-4-oxoquinoline-3-carboxylic acid hemihydrate.

2. A compound represented by the following formula:

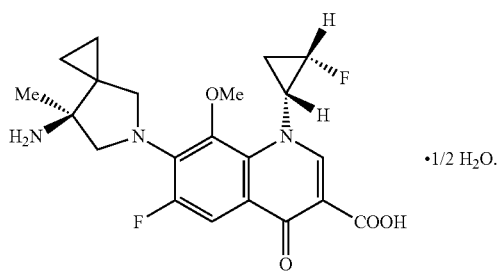

·1/2 $H_2O$.

3. A pharmaceutical composition comprising the compound according to claim 1 and a pharmaceutically acceptable carrier.

4. A method for treating tuberculosis or preventing or treating a bacterial infection, comprising administering to a patient in need thereof an effective amount of the compound according to claim 1 to treat or prevent tuberculosis or a bacterial infection in the patient.

5. The method according to claim 4, wherein tuberculosis is treated.

6. The method according to claim 4, wherein a bacterial infection is treated or prevented.

7. A pharmaceutical composition comprising the compound according to claim 2 and a pharmaceutically acceptable carrier.

8. A method for treating tuberculosis or preventing or treating a bacterial infection, comprising administering to a patient in need thereof an effective amount of the compound according to claim 2 to treat or prevent tuberculosis or a bacterial infection in the patient.

9. The method according to claim 8, wherein tuberculosis is treated.

10. The method according to claim 8, wherein a bacterial infection is treated or prevented.

11. The method according to claim 4, wherein tuberculosis or a bacterial infection is treated.

12. The method according to claim 8, wherein tuberculosis or a bacterial infection is treated.

13. The method according to claim 4, wherein a bacterial infection is prevented.

14. The method according to claim 8, wherein a bacterial infection is prevented.

* * * * *